United States Patent
Shimizu et al.

(10) Patent No.: US 12,402,944 B2
(45) Date of Patent: Sep. 2, 2025

(54) LIGHT RADIATING DEVICE

(71) Applicants: Neuroceuticals Inc., Tokyo (JP); I-PEX Inc., Kyoto (JP)

(72) Inventors: Kazuo Shimizu, Tokyo (JP); Yoichi Goto, Ogori (JP); Toshifumi Matsumoto, Machida (JP); Shoichi Kawamura, Machida (JP)

(73) Assignee: NeuroLightech Inc., Tokyo (JP)

( * ) Notice: Subject to any disclaimer, the term of this patent is extended or adjusted under 35 U.S.C. 154(b) by 338 days.

(21) Appl. No.: 17/261,789

(22) PCT Filed: Jul. 19, 2019

(86) PCT No.: PCT/JP2019/028471
§ 371 (c)(1),
(2) Date: Jan. 20, 2021

(87) PCT Pub. No.: WO2020/017639
PCT Pub. Date: Jan. 23, 2020

(65) Prior Publication Data
US 2021/0259771 A1  Aug. 26, 2021

(30) Foreign Application Priority Data
Jul. 20, 2018 (JP) .................. 2018-137030

(51) Int. Cl.
*A61B 18/20* (2006.01)
*A61B 18/22* (2006.01)
(Continued)

(52) U.S. Cl.
CPC .............. *A61B 18/22* (2013.01); *G02B 6/262* (2013.01); *A61B 2018/00101* (2013.01); *A61B 2018/00595* (2013.01); *A61B 2018/2255* (2013.01)

(58) Field of Classification Search
CPC ............ A61B 18/20; A61N 5/06; A61F 9/008
See application file for complete search history.

(56) References Cited

U.S. PATENT DOCUMENTS 5,370,643 A * 12/1994 Krivoshlykov ...... G02B 6/4296
385/124
5,437,660 A * 8/1995 Johnson ................. A61B 18/24
606/7
(Continued)

FOREIGN PATENT DOCUMENTS

JP  S6211820 A  1/1987
JP  H04285548 A  10/1992
(Continued)

OTHER PUBLICATIONS

"Ellipsoid" Britannica (Year: 2006).*
(Continued)

*Primary Examiner* — Lynsey C Eiseman
(74) *Attorney, Agent, or Firm* — Howard & Howard Attorneys PLLC

(57) ABSTRACT

A light radiating device (1A) performs solidification or cauterization of a biological tissue (PL) by radiating a light beam (BM). A light source (10A) emits the light beam (BM). An optical waveguide (20A) is a member being provided with a reflection surface (21A) totally reflecting the light beam (BM) on an inner circumferential side wall, causing the light beam (BM) emitted from the light source (10A) to enter a part enclosed by the inner circumferential side wall from one end, and sending the light beam (BM) to the other end. A catoptric system (30A) reflects the light beam (BM) sent to the other end of the optical waveguide (20A) and condenses the light beam (BM) on the biological tissue (PL).

13 Claims, 29 Drawing Sheets

(51) Int. Cl.
*G02B 6/26* (2006.01)
*A61B 18/00* (2006.01)

(56) References Cited

U.S. PATENT DOCUMENTS

| | | | | |
|---|---|---|---|---|
| 5,836,941 | A * | 11/1998 | Yoshihara | A61B 18/24 606/17 |
| 6,168,590 | B1 * | 1/2001 | Neev | A61B 18/203 606/9 |
| 6,379,347 | B1 * | 4/2002 | Maki | A61B 18/24 606/17 |
| 6,607,526 | B1 * | 8/2003 | Maki | A61N 5/0601 600/101 |
| 2002/0045811 | A1 | 4/2002 | Kittrell | G02B 6/4296 606/7 |
| 2006/0084958 | A1 * | 4/2006 | Raif | A61B 18/148 606/17 |
| 2007/0282315 | A1 * | 12/2007 | Strassl | A61C 1/052 606/9 |
| 2008/0308753 | A1 | 12/2008 | Stuba et al. | |
| 2011/0087202 | A1 * | 4/2011 | Lewinsky | A61N 5/0603 606/14 |
| 2013/0274726 | A1 * | 10/2013 | Takayama | G02B 6/262 606/15 |
| 2015/0283397 | A1 | 10/2015 | Andersen et al. | |
| 2018/0049806 | A1 * | 2/2018 | Yu | A61B 18/22 |

FOREIGN PATENT DOCUMENTS

| | | | |
|---|---|---|---|
| JP | H0838499 | A | 2/1996 |
| JP | H0951899 | A | 2/1997 |
| JP | 2000-225123 | A | 8/2000 |
| JP | 2005-079197 | A | 3/2005 |
| JP | 2005-177150 | A | 7/2005 |
| JP | 2010-529885 | A | 9/2010 |
| JP | 2017-515530 | A | 6/2017 |
| WO | WO-2016148718 | A1 * | 9/2016 ............ A61B 18/22 |

OTHER PUBLICATIONS

"Paraboloid" Britannica (Year: 2008).*
International Search Report (International Application No. PCT/JP2019/028471); Mail Date: Oct. 8, 2019; 4 pages; Includes English Translation.
Written Opinion (International Application No. PCT/JP2019/028471); Mail Date Oct. 8, 2019; 5 pages.

* cited by examiner

LIGHT RADIATING DEVICE

CROSS-REFERENCE TO RELATED APPLICATIONS

This application is a national phase application of International Patent Application No. PCT/JP2019/028471, filed Jul. 19, 2019, which claims priority to JP Patent Application No. 2018-137030, filed Jul. 20, 2018, the disclosures of which are hereby incorporated by reference in their entirety.

TECHNICAL FIELD

The present disclosure relates to a light radiating device.

BACKGROUND ART

A device enabling solidification or cauterization of a biological tissue is disclosed in Patent Literature 1. In the device, light being output from a halogen light source and propagating through an optical fiber member is output from a metal sleeve provided at one end of the optical fiber member and is radiated to a biological tissue. Resulting generation of heat in the biological tissue enables solidification or cauterization of the biological tissue.

CITATION LIST

Patent Literature

Patent Literature 1: Unexamined Japanese Patent Application Publication (Translation of PCT Application) No. 2010-529885

SUMMARY OF INVENTION

Technical Problem

In the aforementioned device, light output from the metal sleeve is reflected off an inner wall of the optical fiber member and is diffused. Accordingly, heat is generated by the light only around the metal sleeve. Therefore, in order to perform solidification or cauterization of a biological tissue by use of the aforementioned device, the metal sleeve needs to be in tight contact with the biological tissue (radiation target).

The present disclosure has been made in view of the circumstance described above, and the objective thereof is to provide a light radiating device that can perform solidification or cauterization of a radiation target in a state of being kept apart from the radiation target without being in tight contact with the radiation target.

Solution to Problem

In order to achieve the aforementioned objective, a light radiating device according to the present disclosure is a light radiating device performing solidification or cauterization of a radiation target by radiating a light beam, the light radiating device including:
 a light source emitting the light beam;
 an optical waveguide having an inner circumferential side wall provided with a reflection surface totally reflecting the light beam, causing the light beam emitted from the light source to enter a part enclosed by the inner circumferential side wall from one end, and sending the light beam to another end; and
 a catoptric system reflecting the light beam sent to another end of the optical waveguide and condensing the light beam on the radiation target.

In this case, a reflection surface of the catoptric system may condense the reflected light beam with respect to a direction along an incidence plane of a light ray entering from a direction of an optical axis of the optical waveguide.

Further, a sectional shape of a reflection surface of the catoptric system when the reflection surface is cut by an incidence plane of a light ray entering along an optical axis of the optical waveguide may be a concave elliptical arc, and
 a reflection surface of the catoptric system may condense a light ray entering each point on the elliptical arc from a direction of an optical axis of the optical waveguide on a focus of the elliptical arc.

A sectional shape of a reflection surface of the catoptric system when the reflection surface is cut by a plane including an incidence position of a light ray entering along an optical axis of the optical waveguide and being orthogonal to an optical axis of the optical waveguide may be a concave circular arc centered on the focus, and
 a reflection surface of the catoptric system may condense a light ray entering each point on the circular arc from a direction parallel to the optical axis on the focus.

A sectional shape of a reflection surface of the catoptric system when the reflection surface is cut by a plane including an incidence position of a light ray entering along an optical axis of the optical waveguide and being orthogonal to an optical axis of the optical waveguide may be a straight line or a convex curve, and
 a reflection surface of the catoptric system may reflect, toward a linear region including the focus on the radiation target, a light ray entering each point on the straight line or the convex curve from a direction parallel to the optical axis.

A reflection surface of the catoptric system may be formed by a plurality of planes normal line directions of which are different from one another being connected.

A section of a reflection surface of the catoptric system when the reflection surface is cut by a plane orthogonal to an optical axis of the optical waveguide may be a polygonal line.

A section of a reflection surface of the catoptric system when the reflection surface is cut by an incidence plane of a light ray entering along an optical axis of the optical waveguide may be a polygonal line.

When a light ray an emission angle of which from the light source with respect to an optical axis of the optical waveguide is maximum is reflected at a second position on the inner circumferential side wall after being reflected at a first position on the inner circumferential side wall,
 a length of the optical waveguide in a direction of an optical axis may be an integral multiple of a distance between the first position and the second position with respect to the optical axis.

A reflection surface of the optical waveguide may be a surface of a metal material film formed on the inner circumferential side wall, and
 a film made up of silicon dioxide may be formed on a surface of the metal material film.

A thickness of the film made up of silicon dioxide may be ¼ of a wavelength of a part of one or more light rays included in a light beam emitted from the light source.

A first optical condensing system condensing the light beam emitted from the light source and causing the light beam to enter at one end of the optical waveguide may be provided.

A second optical condensing system condensing the light beam emitted from another end of the optical waveguide and causing the light beam to enter the catoptric system may be provided.

A distance from the second optical condensing system to the catoptric system may be greater than a focal distance of the second optical condensing system.

When a sectional shape of a concave reflection surface of the catoptric system when the concave reflection surface is cut by an incidence plane of a light ray entering along an optical axis of the optical waveguide is approximated to a parabola,
 a focus position of the second optical condensing system may be positioned at a focus of the parabola.

The inner circumferential side wall may be formed in a prismatic shape in the optical waveguide.

The optical waveguide may be a hollow tube.

The optical waveguide may be a quartz rod.

A heat insulating part may be provided on an outer periphery of the optical waveguide and the catoptric system.

The heat insulating part may include:
 an exterior cover enclosing an outer periphery of the optical waveguide and the catoptric system; and
 a spacer inserted between the optical waveguide and the catoptric system, and the exterior cover in order to provide a gap between the optical waveguide and the catoptric system, and the exterior cover.

On the spacer, a plurality of projections may be provided on at least one of a part facing the optical waveguide and the catoptric system, and a part facing the exterior cover.

A size of a reflection surface of the catoptric system when the reflection surface is viewed from a direction of an optical axis of the optical waveguide may be equal to or greater than a size of a section of a light beam entering the catoptric system from the optical waveguide.

A light beam emitted from the light source may include an infrared radiation.

The light source may be one of a halogen lamp, a xenon lamp, an infrared heater, and an infrared laser.

Advantageous Effects of Invention

The present disclosure includes a catoptric system reflecting a light beam sent to another end of an optical waveguide and condensing the light beam. The light beam can be thereby condensed at a position apart from the device and can generate intense heat at the position. Consequently, solidification or cauterization of a radiation target can be performed in a state of being kept apart from the radiation target without being in tight contact with the radiation target.

DESCRIPTION OF EMBODIMENTS

Light radiating devices according to embodiments of the present disclosure will be described in detail below with reference to drawings. In every drawing, the same or equivalent components are given the same sign. The light radiating device according to the present embodiment can be considered as an optical scalpel performing solidification or cauterization of a biological tissue in a state of separating the biological tissue being a radiation target from the device.

Embodiment 1

Figure 1:
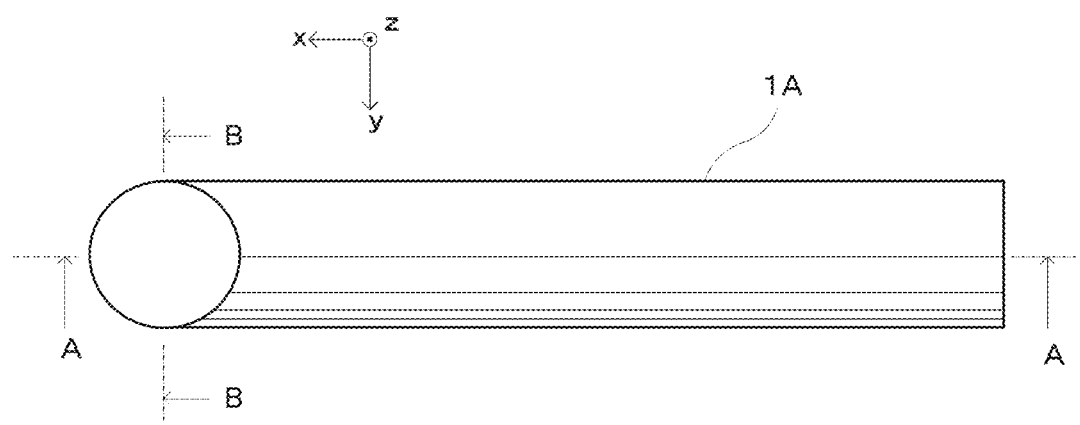
FIG. 1 is a top view illustrating a structure of a light radiating device according to Embodiment 1 of the present disclosure.
Figure 2:
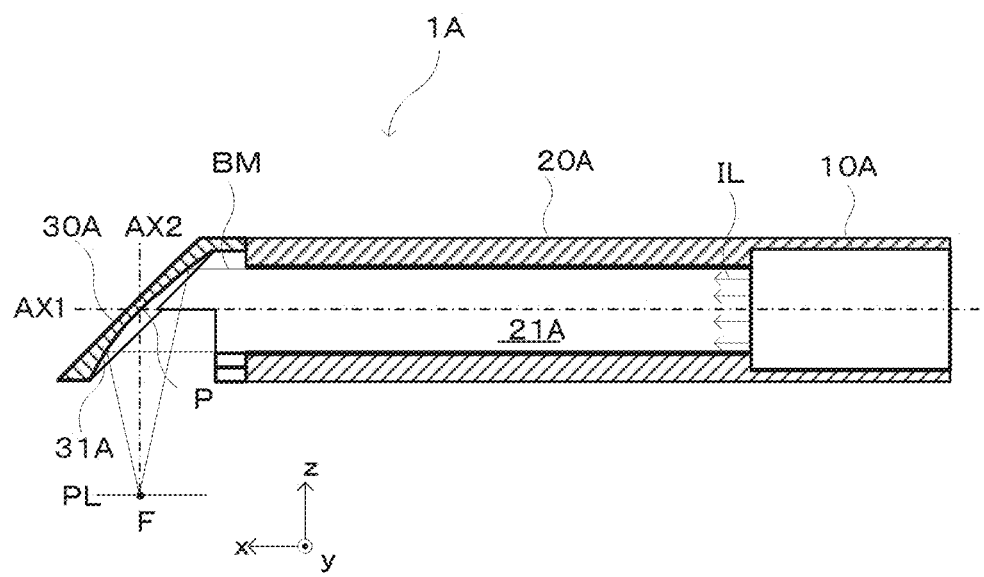
FIG. 2 is a cross-sectional view taken along an A-A line in FIG. 1.

First, Embodiment 1 of the present disclosure will be described. As illustrated in FIG. 1, a light radiating device 1A according to Embodiment 1 is a long and narrow columnar member. As illustrated in FIG. 2, the light radiating device 1A includes a light source 10A, an optical waveguide 20A, and a catoptric system 30A.

The light source 10A is a surface light source and emits alight beam BM being abeam of light rays IL from a part facing one end of the optical waveguide 20A. For example, an infrared laser is used as the light source 10A. Accordingly, a wavelength region of the emitted light beam BM mainly includes the infrared region and more specifically the near-infrared region.

The optical waveguide 20A is an optical member extending in a direction of an optical axis AX1 thereof. The optical waveguide 20A causes the light beam BM emitted from the light source 10A to enter from one end and emits the light beam BM from the other end.

The optical waveguide 20A according to the present embodiment is a tubular (hollow) member and has an inner circumferential side wall. The sectional shape of the optical waveguide 20A is a circle. A reflection surface 21A totally reflecting the light beam BM is provided on the inner circumferential side wall of the optical waveguide 20A. Part of the light beam BM emitted from the light source 10A enters a part enclosed by the inner circumferential side wall (reflection surface 21A) and is sent to the other end while being totally reflected off the reflection surface 21A. An enclosure of the optical waveguide 20A is formed of metal or resin, and the reflection surface 21A is a surface of a film formed by depositing metal such as aluminum on the inner circumferential side wall.

The catoptric system 30A reflects the light beam BM sent to the other end of the optical waveguide 20A and condenses the light beam BM on a focus F on an optical axis AX2. Specifically, a reflection surface 31A of the catoptric system 30A condenses the reflected light beam BM with respect to an x-axis direction along an incidence plane of a light ray IL entering from a direction of the optical axis AX1 of the optical waveguide 20A. An enclosure of the catoptric system 30A is formed of metal or resin, and the reflection surface 31A is formed by depositing metal such as aluminum.

Figure 3:
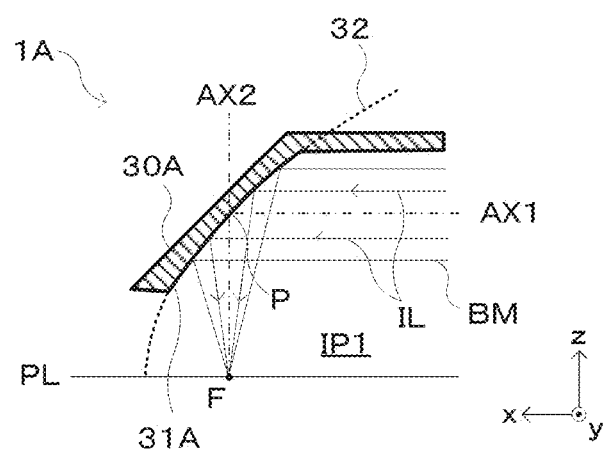
FIG. 3 is an expanded sectional view of a catoptric system along the optical axis of an optical waveguide.
Figure 4:
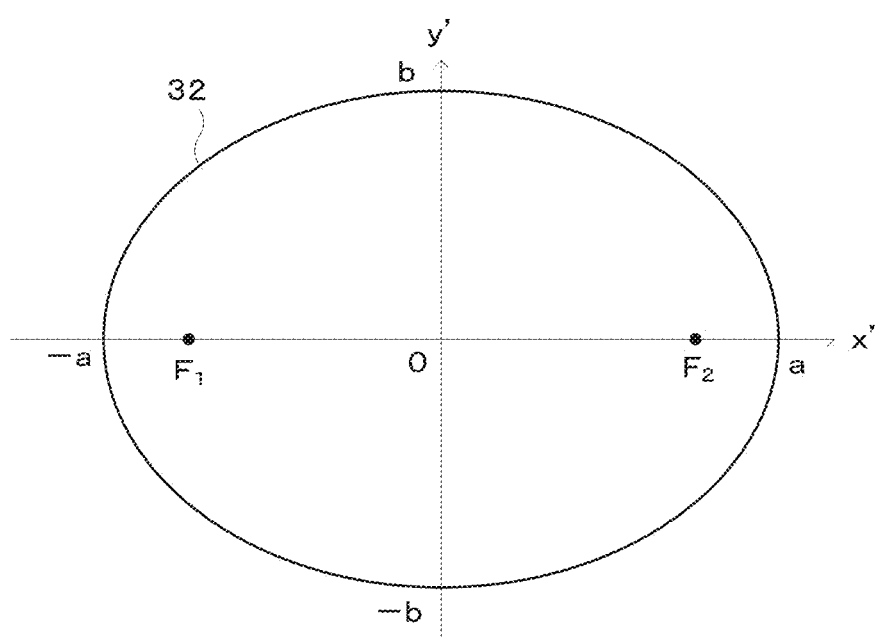
FIG. 4 is a schematic diagram of an ellipse.

In the catoptric system 30A, the sectional shape of the reflection surface 31A when the reflection surface is cut by an incidence plane IP1 of a light ray entering along the optical axis AX1 of the optical waveguide 20A (a sectional shape along the x-axis direction) is a concave elliptical arc 32, as illustrated in FIG. 3. The elliptical arc 32 is part of an ellipse as illustrated in FIG. 4. In the ellipse in FIG. 4, the length of the major axis along an x'-axis direction is denoted by $2a$, and the length of the minor axis along a y'-axis direction is denoted by $2b$. The foci of the ellipse are denoted by $F_1$ and $F_2$. At this time, light parallel to the x'-axis direction is condensed on the focus $F_1$ or $F_2$ of the ellipse.

The reflection surface 31A condenses a light ray IL entering each point on the elliptical arc 32 from the direction of the optical axis AX1 of the optical waveguide 20A on a focus F of the elliptical arc 32. The focus F matches the focus $F_1$ or $F_2$ of the ellipse illustrated in FIG. 4.

Figure 5:
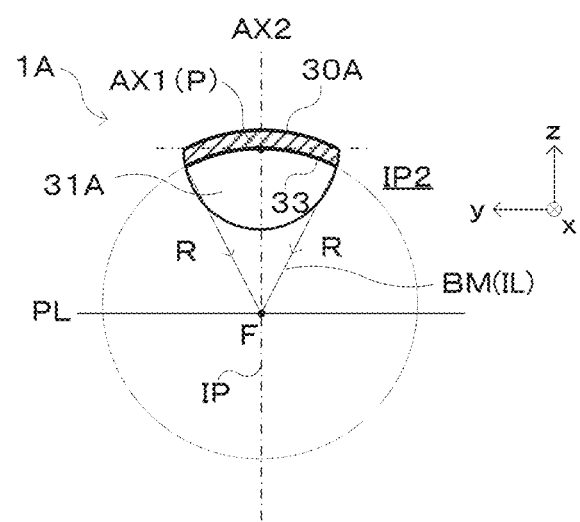
FIG. 5 is a cross-sectional view taken along a B-B line in FIG. 1.

Further, in the catoptric system 30A, the sectional shape of the reflection surface 31A when the reflection surface 31A is cut by a plane IP2 including an incidence position P of a light ray IL entering along the optical axis AX1 of the optical waveguide 20A and being orthogonal to the optical axis AX1 of the optical waveguide 20A is a concave circular arc 33 centered on the focus F, as illustrated in FIG. 5. The reflection surface 31A condenses alight ray IL entering each point on the circular arc 33 from a direction parallel to the optical axis AX1 on the focus F. A radius R of the circular arc 33 is determined in such a way that a light ray IL is condensed on the focus F.

Figure 6:
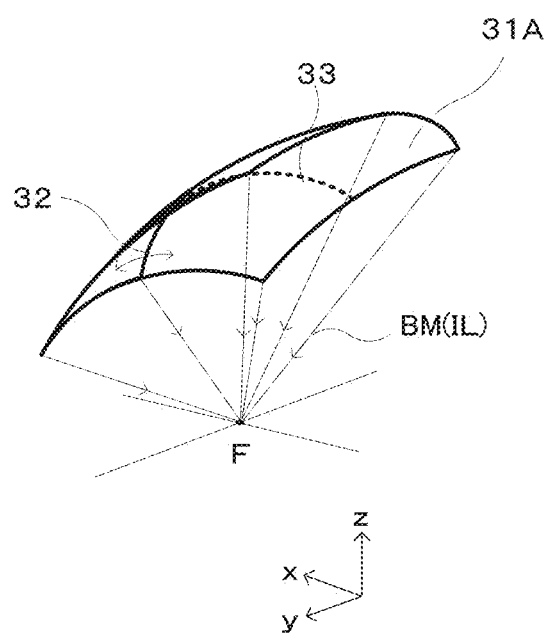
FIG. 6 is a schematic diagram illustrating the three-dimensional shape of a reflection surface.

As described above, the sectional shape of the reflection surface 31A of the catoptric system 30A along the x-axis direction is the elliptical arc 32, and the sectional shape along a y-axis direction is the circular arc 33. The three-dimensional shape of the reflection surface 31A having such sectional shapes is as illustrated in FIG. 6. The three-dimensional shape of the reflection surface 31A is a curved surface formed when each point on the elliptical arc 32 is rotated around the focus F. Every light ray IL entering in the x-axis direction is thereby condensed on the focus F. Note that the outline of the reflection surface 31A is assumed to be a rectangle in FIG. 6.

Thus, in the light radiating device 1A according to the present embodiment, out of light rays IL constituting the light beam BM emitted from the light source 10A, a light ray IL traveling in parallel with the optical axis AX1 is condensed on the focus F.

Figure 7:
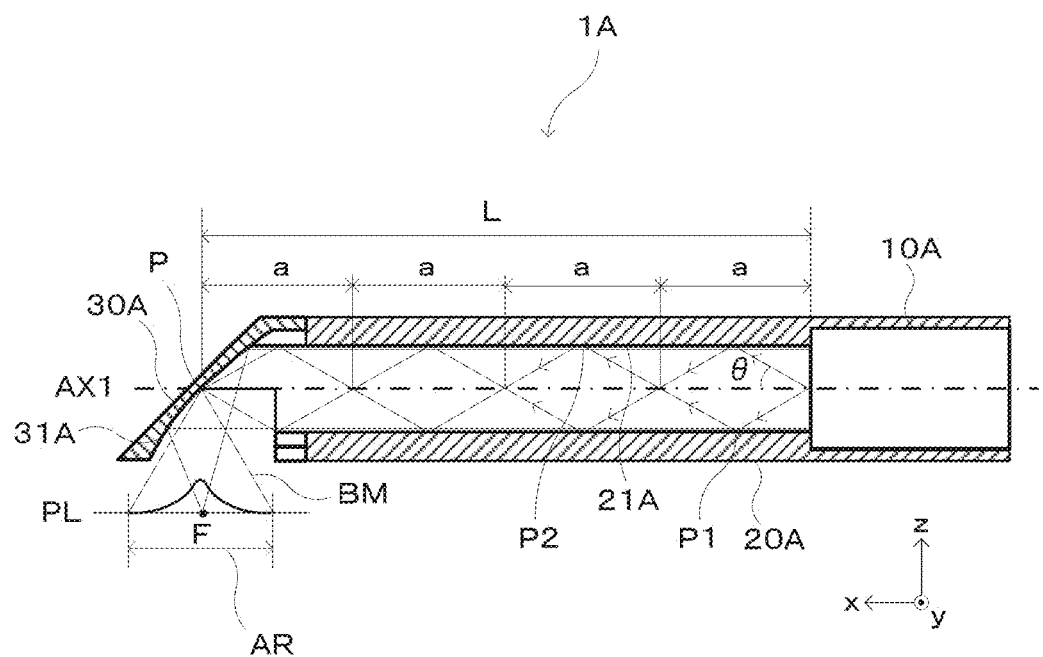
FIG. 7 is a diagram illustrating the length of the optical waveguide in the optical axis direction.

In practice, light rays IL emitted from the light source 10A do not necessarily travel along the optical axis AX1 and travel in such a way as to diffuse from each point of the light source 10A. As illustrated in FIG. 7, the maximum emission angle of a light ray IL with respect to the optical axis AX1 of the optical waveguide 20A is denoted by θ. For example, θ is 30 degrees.

It is assumed here that a light ray IL the emission angle of which from the light source 10A with respect to the optical axis AX1 of the optical waveguide 20A is the maximum emission angle θ is reflected at a second position P2 on the reflection surface 21A after being reflected at a first position P1 on the reflection surface 21A, as illustrated in FIG. 7. In this case, it is assumed in the present embodiment that the length of the optical waveguide 20A in the optical axis AX1 direction is a length L being four times a distance a between the first position P1 and the second position P2 with respect to the optical axis AX1.

A light ray IL emitted from the light source 10A in a diffusing manner enters, in the x-axis direction, a region AR centered on the focus F on a biological tissue PL being a radiation target. Since the length L of the optical waveguide 20A in the optical axis AX1 direction is an integral multiple of the distance a, intensity of the light ray IL entering the region AR is maximum at the focus F and gradually decreases as the distance from the focus F increases. An intensity distribution of the light ray IL on the biological tissue PL is rotationally symmetric around the focus F.

Thus, the light radiating device 1A according to the present embodiment condenses the light beam BM on the focus F in the x-axis direction and the y-axis direction. Light intensity on the focus F is thereby increased, and a heating value increases. Consequently, solidification or cauterization the biological tissue PL being the radiation target at the focus F can be performed.

Embodiment 2

Figure 8A:
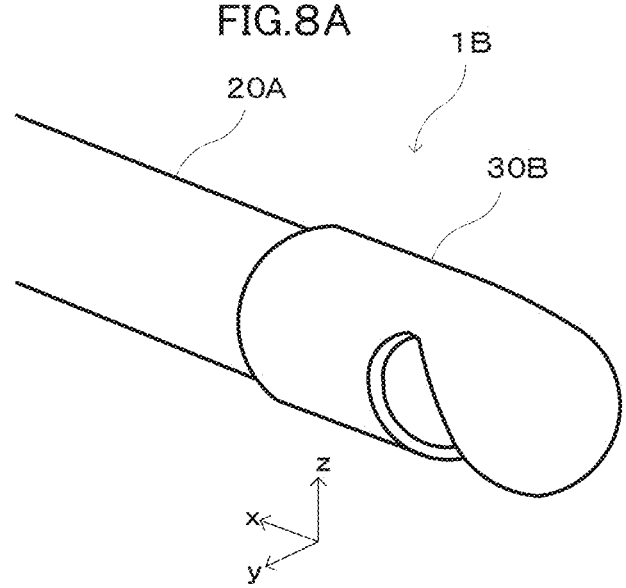
FIG. 8A is a perspective view illustrating a partial structure of a light radiating device according to Embodiment 2 of the present disclosure.
Figure 8B:
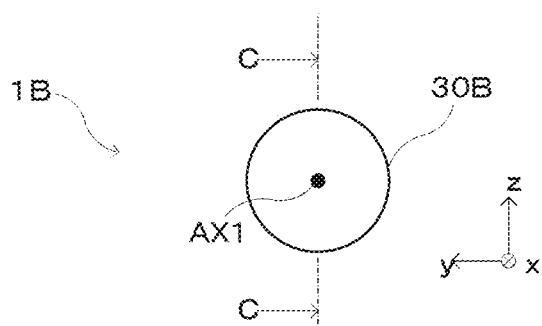
FIG. 8B is a front view of the light radiating device in FIG. 8A.
Figure 8C:
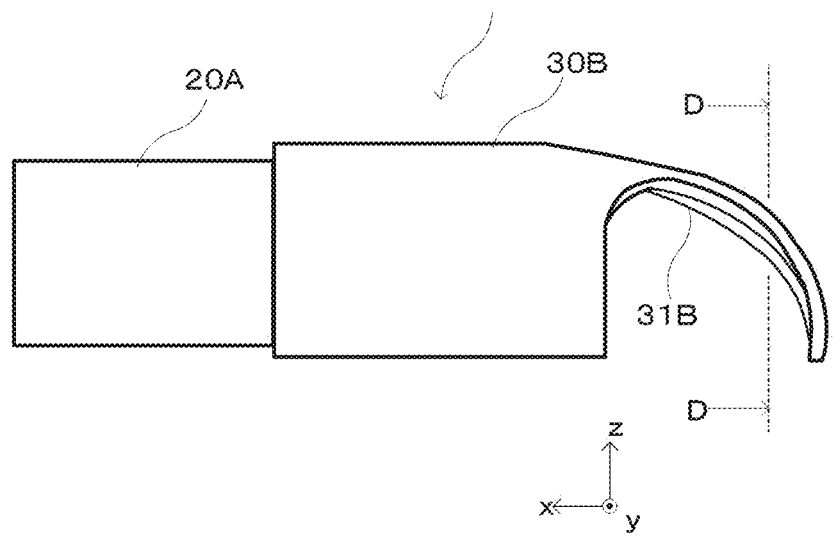
FIG. 8C is a side view illustrating a partial structure of the light radiating device in FIG. 8A.

Next, Embodiment 2 of the present disclosure will be described. A light radiating device 1B according to the present embodiment differs from the light radiating device 1A according to aforementioned Embodiment 1 in including a catoptric system 30B in place of the catoptric system 30A, as illustrated in FIG. 8A, FIG. 8B, and FIG. 8C.

Figure 9:
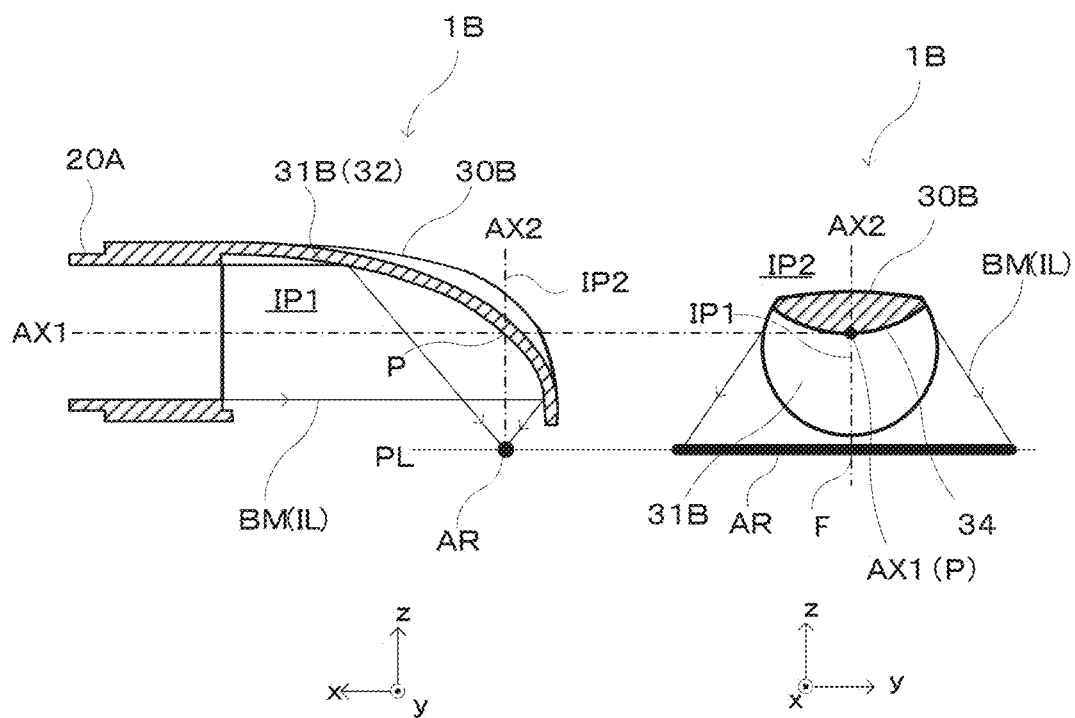
FIG. 9 is a cross-sectional view taken along a C-C line in FIG. 8B and a cross-sectional view taken along a D-D line in FIG. 8C.

As illustrated in FIG. 9, a characteristic that a reflection surface 31B of the catoptric system 30B condenses a reflected light beam BM with respect to an x-axis direction along an incidence plane of a light ray IL entering from a direction of an optical axis AX1 of an optical waveguide 20A in the light radiating device 1B according to the present embodiment is the same as that of the catoptric system 30A according to aforementioned Embodiment 1.

Specifically, in the catoptric system 30B, the sectional shape of the reflection surface 31B when the reflection surface 31B is cut by an incidence plane IP1 of a light ray entering along the optical axis AX1 of the optical waveguide 20A is a concave elliptical arc 32, as illustrated in FIG. 9, similarly to the catoptric system 30A.

However, in the catoptric system 30B according to the present embodiment, the sectional shape of the reflection surface 31B when the reflection surface 31B is cut by a plane IP2 including an incidence position P of a light ray IL entering along the optical axis AX1 of the optical waveguide 20A and being orthogonal to the optical axis AX1 of the optical waveguide 20A is a convex curve (circular arc 34), as illustrated in FIG. 9. The reflection surface 31B reflects, toward a linear region AR including a focus F on a biological tissue PL being a radiation target, a light ray IL entering each point on the convex curve (circular arc 34) from a direction parallel to the optical axis AX1 of the optical waveguide 20A.

The sectional shape of the reflection surface 31B along a y-axis direction orthogonal to the x-axis direction may be a straight line, according to the present embodiment. Even in such a case, the sectional shape of the light beam BM on the biological tissue PL being the radiation target is the linear region AR.

Figure 10:
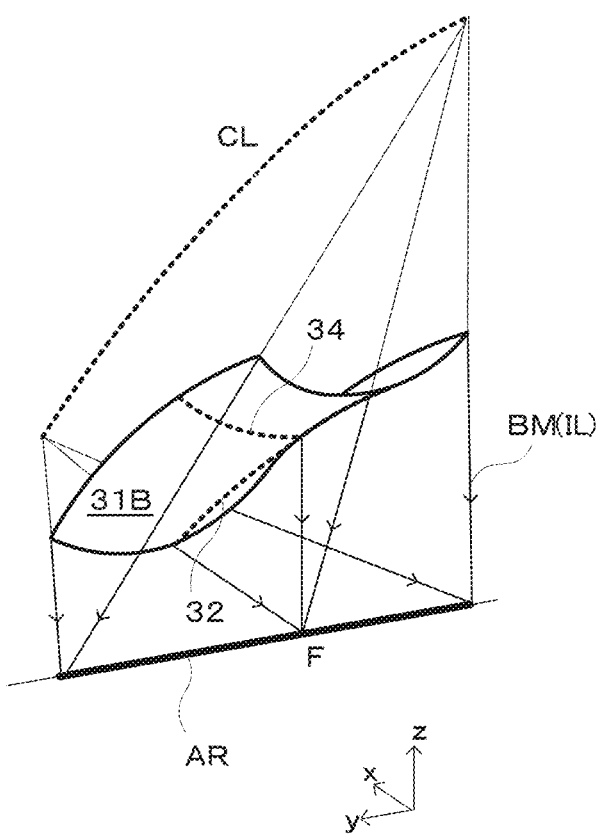
FIG. 10 is a schematic diagram illustrating the three-dimensional shape of a reflection surface.

As described above, the sectional shape of the reflection surface 31B of the catoptric system 30B along the x-axis direction is the elliptical arc 32, and the sectional shape along the y-axis direction is the circular arc 34. The three-dimensional shape of the reflection surface 31B having such sectional shapes is as illustrated in FIG. 10. A curve CL (a curve similar to the elliptical arc 32) projecting the elliptical arc 32 viewed from the center (focus F) of the linear region AR on the biological tissue PL is defined as illustrated in FIG. 10. Then, a curved surface formed when rotating each point on the elliptical arc 32 around the intersection of a straight line connecting each point on the elliptical arc 32 and the focus F, and the curve CL is the reflection surface 31B. Note that the outline of the reflection surface 31B is assumed to be a rectangle in FIG. 10.

Thus, the light radiating device 1B according to the present embodiment condenses the light beam BM on the linear region AR. Light intensity on the region AR is thereby increased, and a heating value increases. Consequently, solidification or cauterization of the biological tissue PL being a radiation target can be performed.

Figure 11:
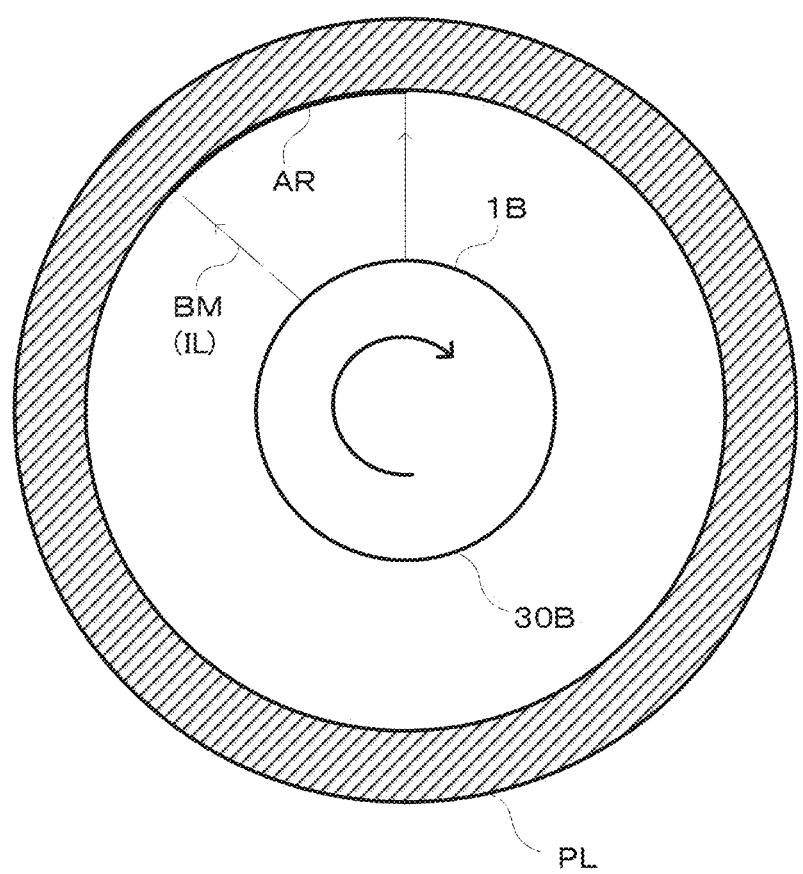
FIG. 11 is a schematic diagram illustrating a case of performing solidification or cauterization of a tubular biological tissue.

For example, the light radiating device 1B according to the present embodiment is suitable for performing solidification or cauterization of an inner circumferential wall of a tubular biological tissue PL along the circumference, as illustrated in FIG. 11.

Embodiment 3

Figure 12A:
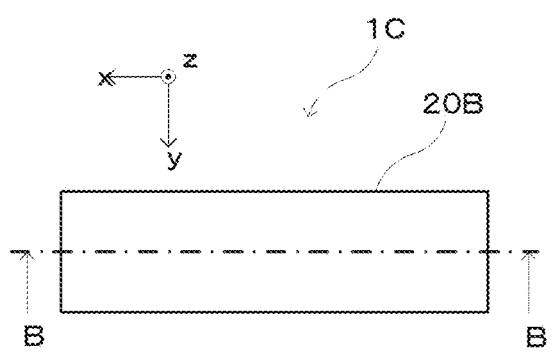
FIG. 12A is a first diagram illustrating a structure of an optical waveguide constituting a light radiating device according to Embodiment 3 of the present disclosure.
Figure 12B:
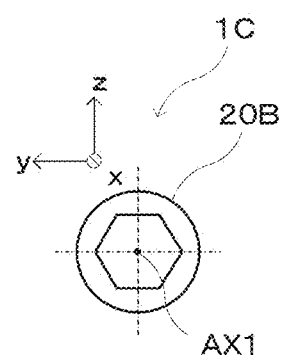
FIG. 12B is a second diagram illustrating the structure of the optical waveguide constituting the light radiating device according to Embodiment 3 of the present disclosure.
Figure 12C:
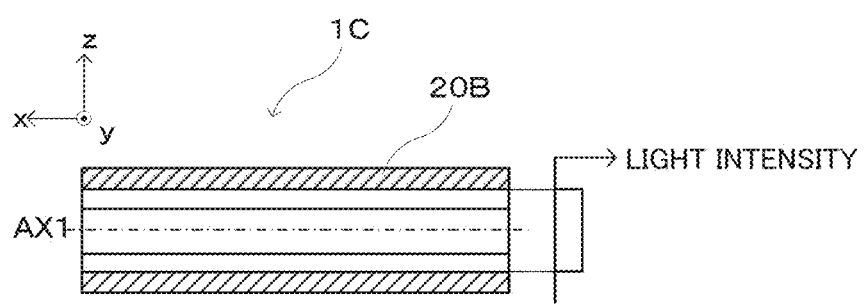
FIG. 12C is a third diagram illustrating the structure of the optical waveguide constituting the light radiating device according to Embodiment 3 of the present disclosure.

Next, Embodiment 3 of the present disclosure will be described. A light radiating device 1C according to the present embodiment differs from the light radiating devices 1A and 1B according to the aforementioned embodiments in using an optical waveguide 20B in place of the optical waveguide 20A, as illustrated in FIG. 12A, FIG. 12B, and FIG. 12C.

An inner circumferential side wall of the optical waveguide 20B is formed in a prismatic shape. For example, the section of the inner circumferential side wall is a hexagon, as illustrated in FIG. 12B.

Figure 13A:
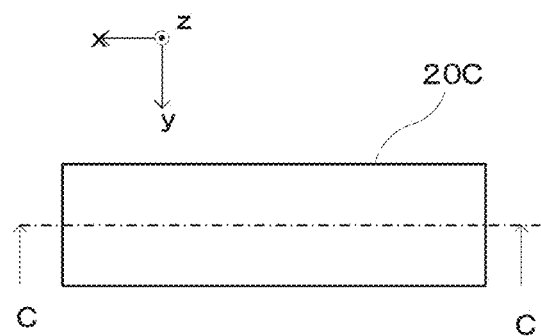
FIG. 13A is a first diagram illustrating a structure of an optical waveguide the sectional shape of which is a circle.
Figure 13B:
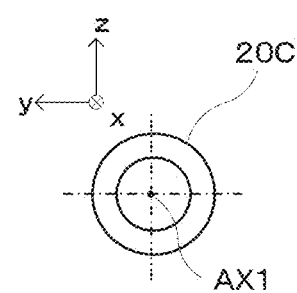
FIG. 13B is a second diagram illustrating the structure of the optical waveguide the sectional shape of which is a circle.
Figure 13C:
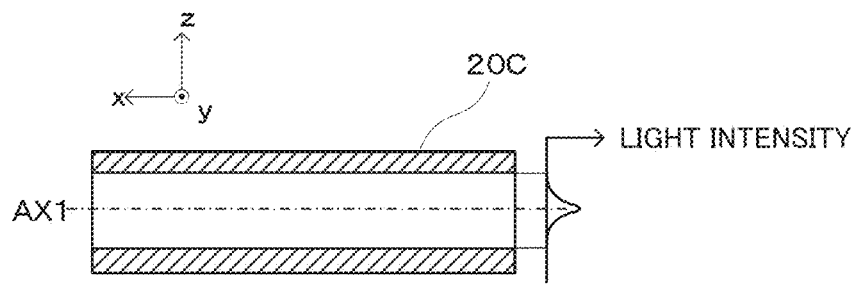
FIG. 13C is a cross-sectional view taken along a C-C line in FIG. 13A.

FIG. 13A, FIG. 13B, and FIG. 13C illustrate an optical waveguide 20C having the same diameter as the optical waveguide 20B, the section of the optical waveguide 20C being a circle. As comparison between a light intensity distribution in FIG. 12C and a light intensity distribution in FIG. 13C tells, forming the optical waveguide 20B in a prismatic shape allows a light intensity distribution of the output light beam BM to be more uniform compared with the optical waveguide 20C the section of which is a circle.

The light radiating device 1C according to the present embodiment may include the catoptric system 30A or may include the catoptric system 30B.

Embodiment 4

Figure 14:
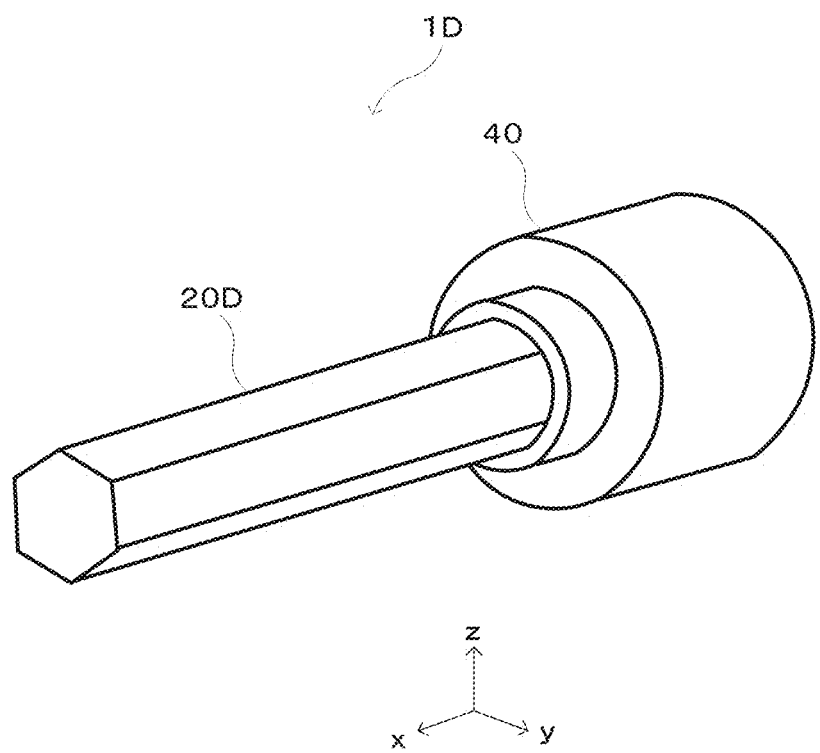
FIG. 14 is a perspective view illustrating a partial structure of a light radiating device according to Embodiment 4 of the present disclosure.

Next, Embodiment 4 of the present disclosure will be described. A light radiating device 1D according to the present embodiment differs from the light radiating device 1A according to aforementioned Embodiment 1 in using an optical waveguide 20D in place of the optical waveguide 20A, as illustrated in FIG. 14. Furthermore, the optical waveguide 20D according to the present embodiment is not directly connected to a light source 10A and is connected through an optical fiber 40.

While each of the optical waveguides 20A, 20B, and 20C according to the aforementioned embodiments is a tubular optical member, the optical waveguide 20D according to the present embodiment is a quartz rod, as illustrated in FIG. 14. The quartz rod also allows causing a light beam BM emitted from the light source 10A to enter from one end through the optical fiber 40, totally reflecting the light beam BM off an inner circumferential side wall, and emitting the light beam BM from the other end. Note that illustration of a catoptric system 30A is omitted in FIG. 14.

The refractive index and the width of the optical waveguide 20D needs to be set in such a way that a light ray IL satisfies a total reflection condition with respect to the maximum emission angle θ from the light source 10A.

While the sectional shape of the optical waveguide 20D is a hexagon, the sectional shape may be a triangle, a rectangle, or a circle.

However, intensity of a light ray IL emitted from the light source 10A attenuates more in the quartz rod compared with a hollow tubular member. Therefore, when an intensive light beam BM is required, it is desirable to use the hollow tubular optical waveguide 20A or 20B.

The light radiating device 1D according to the present embodiment may include the catoptric system 30A or may include the catoptric system 30B.

Embodiment 5

Figure 15A:
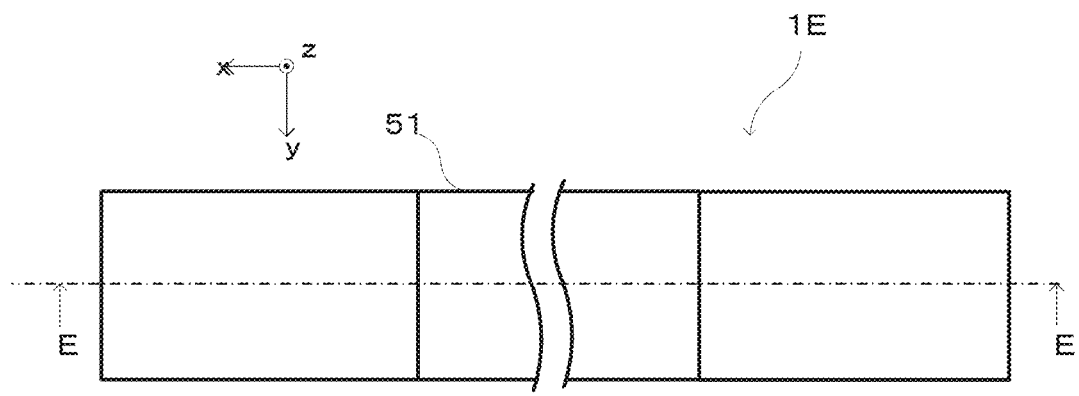
FIG. 15A is a top view illustrating a structure of a light radiating device according to Embodiment 5 of the present disclosure.
Figure 15B:
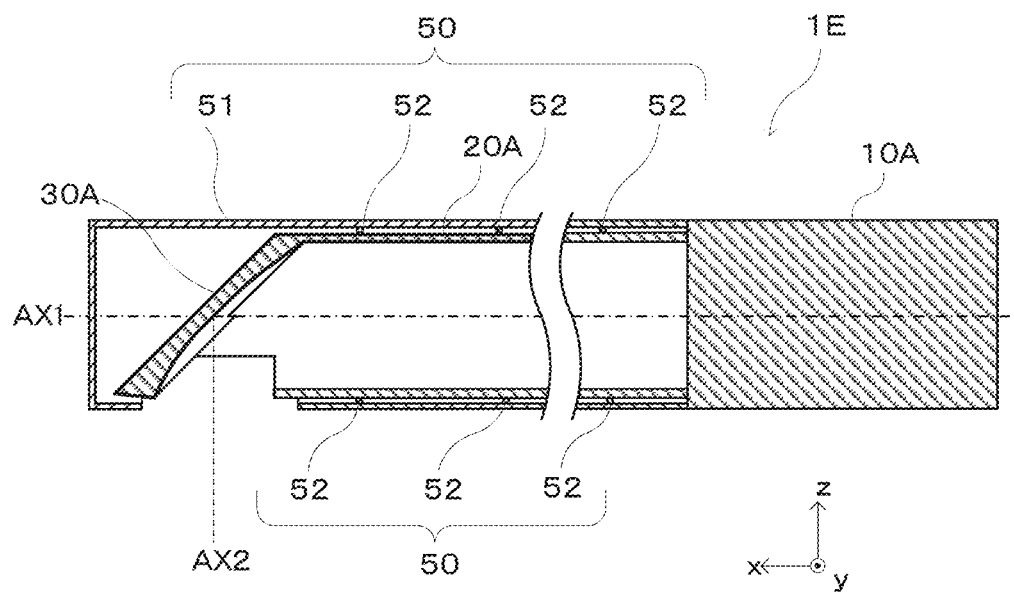
FIG. 15B is a cross-sectional view taken along an E-E line in FIG. 15A.

Next, Embodiment 5 of the present disclosure will be described. As illustrated in FIG. 15B being a cross-sectional view taken along an E-E line in FIG. 15A, a light radiating device 1E according to the present embodiment differs from each of the aforementioned embodiments in including a heat insulating part 50.

The heat insulating part 50 is provided on an outer periphery of an optical waveguide 20A and a catoptric system 30A. The heat insulating part 50 includes an exterior cover 51 and a spacer 52.

The exterior cover 51 encloses the outer periphery of the optical waveguide 20A and the catoptric system 30A. The spacer 52 is inserted between the optical waveguide 20A and the catoptric system 30A, and the exterior cover 51 in order to provide a gap between the optical waveguide 20A and the catoptric system 30A, and the exterior cover 51.

Heat is generated in the optical waveguide 20A and the catoptric system 30A when alight beam BM is reflected. It is undesirable that the heat be transferred to a surrounding biological tissue not being a radiation target. Then, the light radiating device 1E according to the present embodiment provides heat insulation by an air layer formed by the exterior cover 51 and the spacer 52 and suppresses heat transfer to the surrounding biological tissue.

Figure 16:
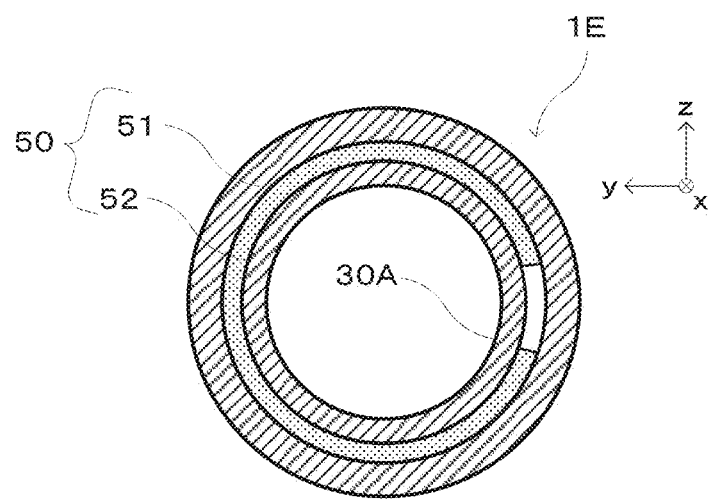
FIG. 16 is a cross-sectional view illustrating a shape of a spacer.

As illustrated in FIG. 16, the spacer 52 is a C-shaped member and allows heat insulating air between the catoptric system 30A and the exterior cover 51 to move inside. Therefore, the heat insulation effect can be enhanced by recovery and supply of the heat insulating air, that is, air circulation.

Figure 17:
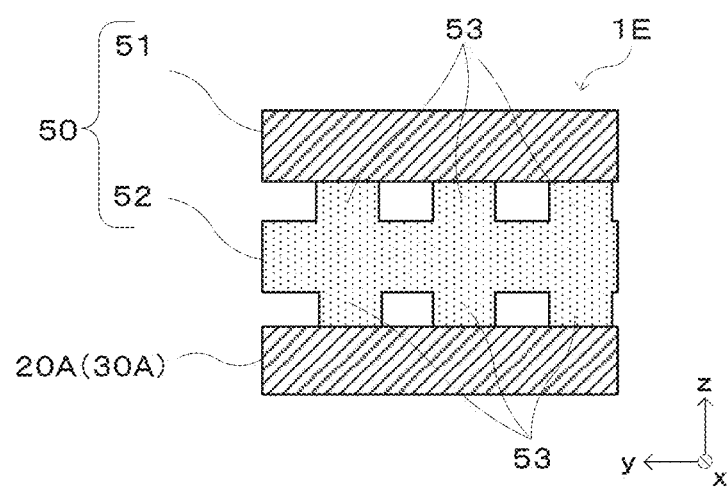
FIG. 17 is a cross-sectional view illustrating a modified example (1) of the shape of the spacer.

Various shapes may be considered as the shape of the spacer 52. For example, a plurality of projections 53 may be provided on a part facing the optical waveguide 20A and the catoptric system 30A, and a part facing the exterior cover 51 on the spacer 52, as illustrated in FIG. 17. Thus, a contact area between the spacer 52, and the optical waveguide 20A and the catoptric system 30A, and a contact area between the spacer 52 and the exterior cover 51 can be reduced, and the heat insulation effect can be enhanced. In this case, the projections 53 may be provided on at least one of the part facing the optical waveguide 20A and the catoptric system 30A, and the part facing the exterior cover 51.

Figure 18:
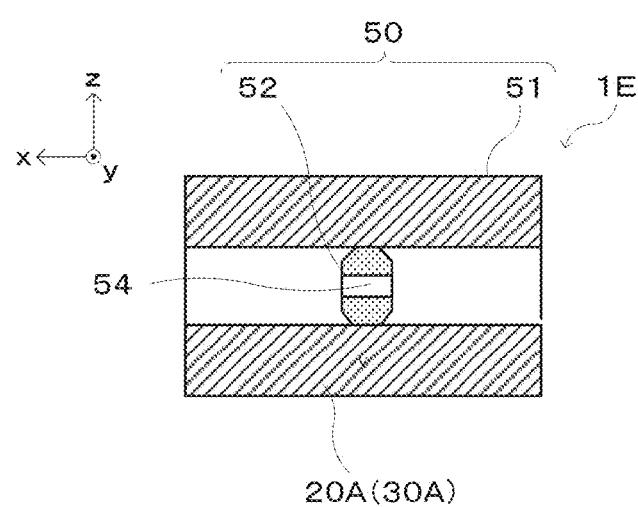
FIG. 18 is a cross-sectional view illustrating a modified example (2) of the shape of the spacer.

Further, the part facing the optical waveguide 20A and the catoptric system 30A, and the part facing the exterior cover 51 on the spacer 52 may be narrowed, as illustrated in FIG. 18. Such narrowing can also reduce the contact area between the spacer 52, and the optical waveguide 20A and the catoptric system 30A, and the contact area between the spacer 52 and the exterior cover 51, and enhance the heat insulation effect.

Further, a through hole 54 may be provided in the spacer 52, as illustrated in FIG. 18. A path of the heat insulating air can be formed by the through hole 54.

It is desirable that the exterior cover 51 and the spacer 52 be formed of a material with low heat conductivity. For example, biocompatible materials such as titan may be used as a material of the exterior cover 51 and the spacer 52.

Heat insulation by an air layer is provided in the present embodiment. In this case, as described above, heat insulation may be provided by circulating air in the air layer. Further, a refrigerant may be inserted in the gap, and the refrigerant may be circulated.

The light radiating device 1E according to the present embodiment may include the catoptric system 30B.

Embodiment 6

Figure 19:
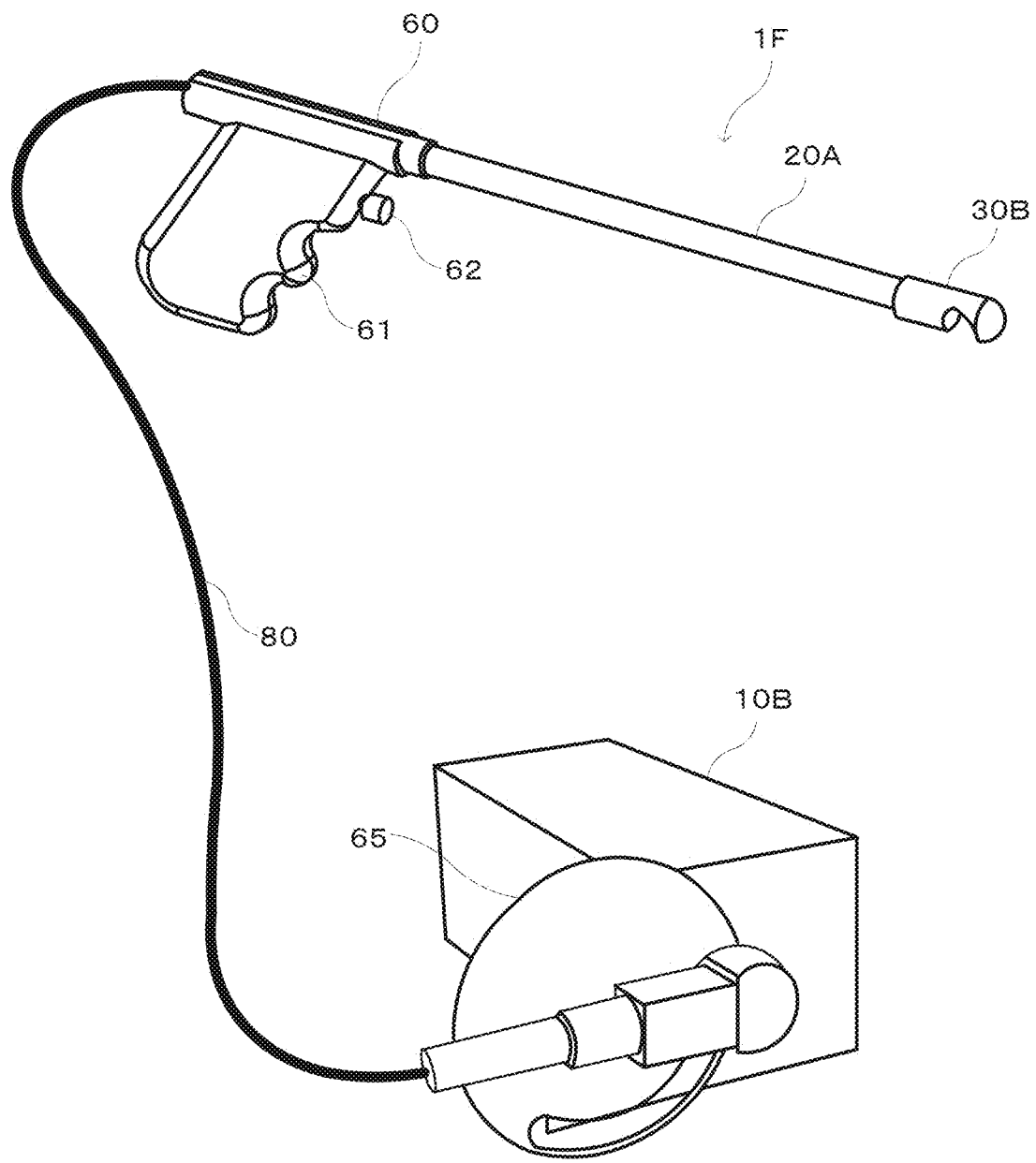
FIG. 19 is a perspective view illustrating a structure of a light radiating device according to Embodiment 6 of the present disclosure.

Next, Embodiment 6 of the present disclosure will be described. A light radiating device 1F according to the present embodiment differs from aforementioned Embodiment 1 in a light source 10B not being directly connected to an optical waveguide 20A, as illustrated in FIG. 19.

The light radiating device 1F according to the present embodiment includes the light source 10B and a rod-shaped operation device 60. The light source 10B is a halogen lamp, a xenon lamp, or an infrared heater. A shutter 65 is mounted on the light source 10B, and rotation of the shutter 65 allows a pulse-shaped light beam BM to be output from the light source 10B.

The optical waveguide 20A and a catoptric system 30B are provided inside the operation device 60. The light source 10B is connected to the operation device 60 by an optical fiber 80. A light beam emitted from the light source 10B is sent to the optical waveguide 20A through the optical fiber 80, is reflected by the catoptric system 30B, and is radiated to a biological tissue PL being a radiation target.

The operation device 60 is provided with a grip 61 and a switch 62. An operator holds the grip 61 and operates the light radiating device 1F. The switch 62 is a switch for turning on and off output of the light beam BM radiated from the light radiating device 1F. The optical waveguide 20A and the catoptric system 30B are extendable and rotatable with respect to the operation device 60. A position of a focus F or a region AR can be thereby adjusted according to a part being a radiation target.

After the adjustment, the operator holds the grip 61, turns on the switch 62 while adjusting the focus F of the catoptric system 30B to a part being a radiation target, and radiates the light beam BM to the part.

The light radiating device 1F according to the present embodiment may include the optical waveguide 20B, 20C, or 20D in place of the optical waveguide 20A. Further, the light radiating device 1F may include the catoptric system 30A in place of the catoptric system 30B. Further, the light radiating device 1F may include the heat insulating part 50.

Embodiment 7

Next, Embodiment 7 of the present disclosure will be described. In each of the light radiating devices 1A to 1F according to the aforementioned embodiments, the shape of the reflection surface of the catoptric system 30A or 30B is a curved surface. Such a reflection surface requires highly skilled manufacturing and also requires highly skilled evaluation of the reflection surface after manufacturing. Then, the present embodiment provides a light radiating device including a reflection surface not requiring highly skilled manufacturing and highly skilled evaluation.

Figure 20:
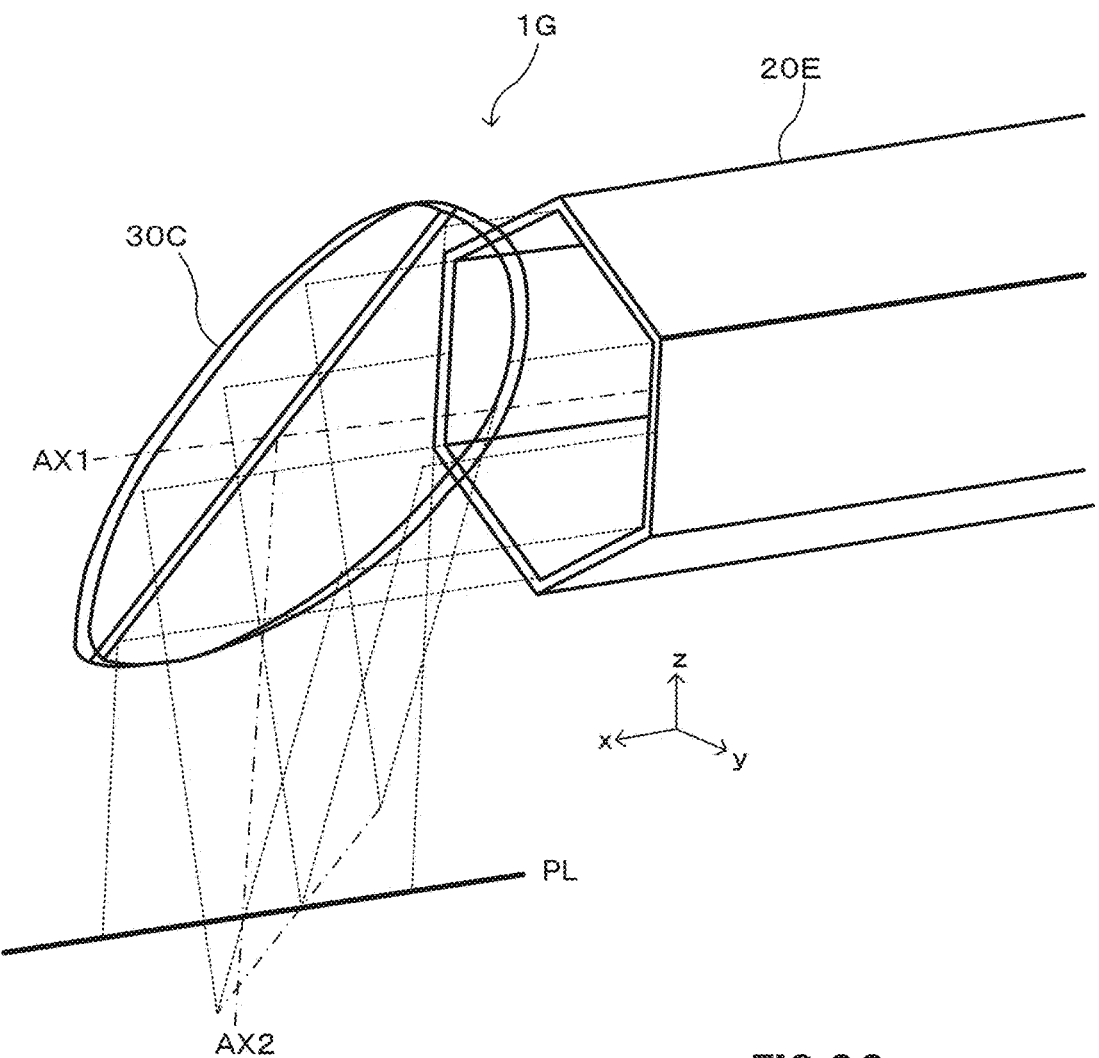
FIG. 20 is a perspective view illustrating a structure of a light radiating device according to Embodiment 7 of the present disclosure.

A light radiating device 1G according to the present embodiment includes an optical waveguide 20E and a catoptric system 30C, as illustrated in FIG. 20. The optical waveguide 20E is a tubular member the section of which is a hexagon, but without being limited thereto, the optical waveguide according to each of the aforementioned embodiments may be used. The light source according to each of the aforementioned embodiments may also be used.

The shape of a reflection surface of the catoptric system 30C in the light radiating device 1G according to the present embodiment differs from that according to each of the aforementioned embodiments. The reflection surface of the catoptric system 30C is formed by connecting a plurality of planes the normal line directions of which are different from one another.

Figure 21:
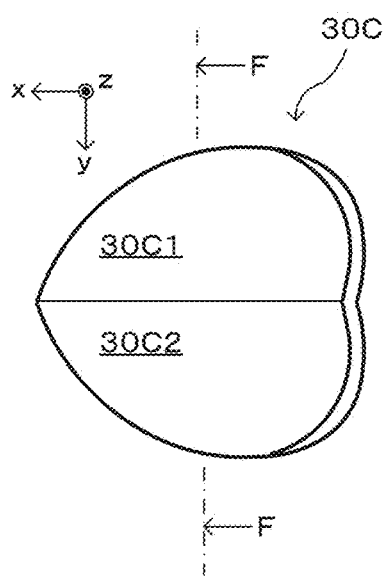
FIG. 21 is a diagram of a catoptric system in FIG. 20 viewed from the +z-direction.
Figure 22:
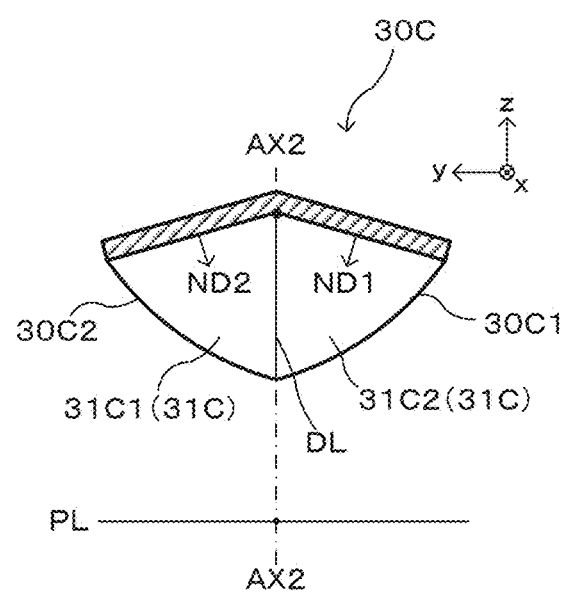
FIG. 22 is a cross-sectional view taken along an F-F line in FIG. 21.

As illustrated in FIG. 21, the catoptric system 30C includes a plane mirror 30C1 and a plane mirror 30C2. As illustrated in FIG. 22, each of a reflection surface 31C1 of the plane mirror 30C1 and a reflection surface 31C2 of the plane mirror 30C2 is a plane. The reflection surface 31C1 and the reflection surface 31C2 are connected by a connecting line DL parallel to an x-z plane in a state of a normal line direction ND1 and a normal line direction ND2 of the respective reflection surfaces being different from each other and more specifically in a state of an angle formed between the reflection surface 31C1 and the reflection surface 31C2 being less than 180°. The sectional shape of a reflection surface 31C when the reflection surface 31C is cut by a y-z plane orthogonal to an optical axis AX1 of the optical waveguide 20E thereby becomes a concave polygonal line shape. The catoptric system 30C condenses an entering light ray with respect to a light beam in a y-axis direction.

A cauterization characteristic of a biological tissue PL will be compared between the light radiating device 1G using the catoptric system 30C (a polygonal plane mirror) according to the present embodiment and a light radiating device using a concave surface approximated to the reflection surface 31C of the light radiating device 1G as a reflection surface. The length of the optical waveguide 20E is assumed to be the same (such as 100 mm) between the two devices.

Figure 23:
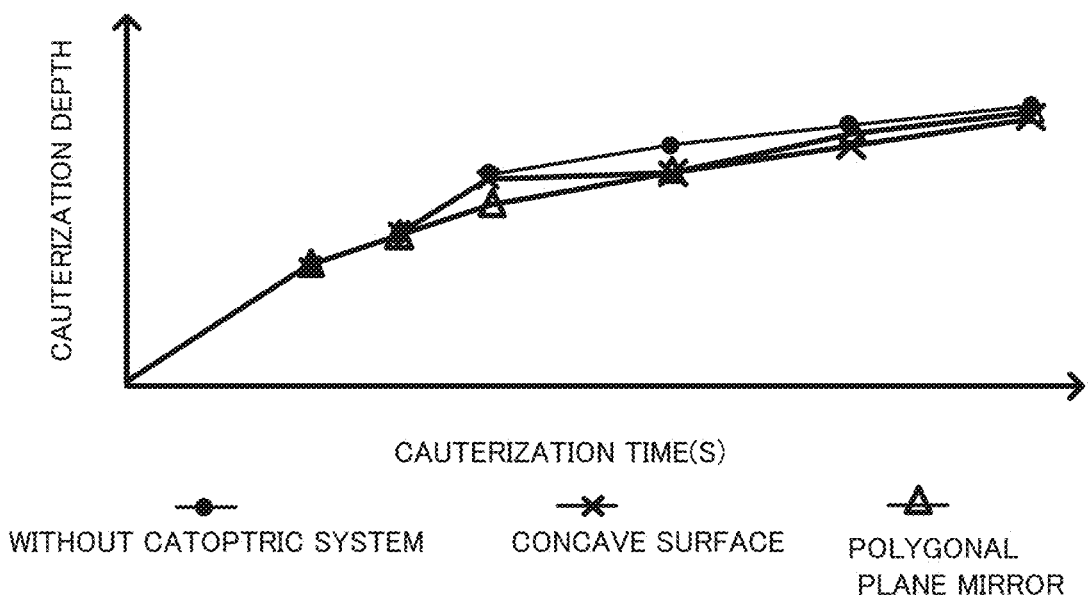
FIG. 23 is a graph illustrating changes in a cauterization depth with respect to cauterization time.

As illustrated in FIG. 23, changes in a cauterization depth of the biological tissue PL change parabolically with respect to cauterization time. The rate of change is almost the same between the case of using the polygonal plane mirror and the case of using the concave surface.

Figure 24:
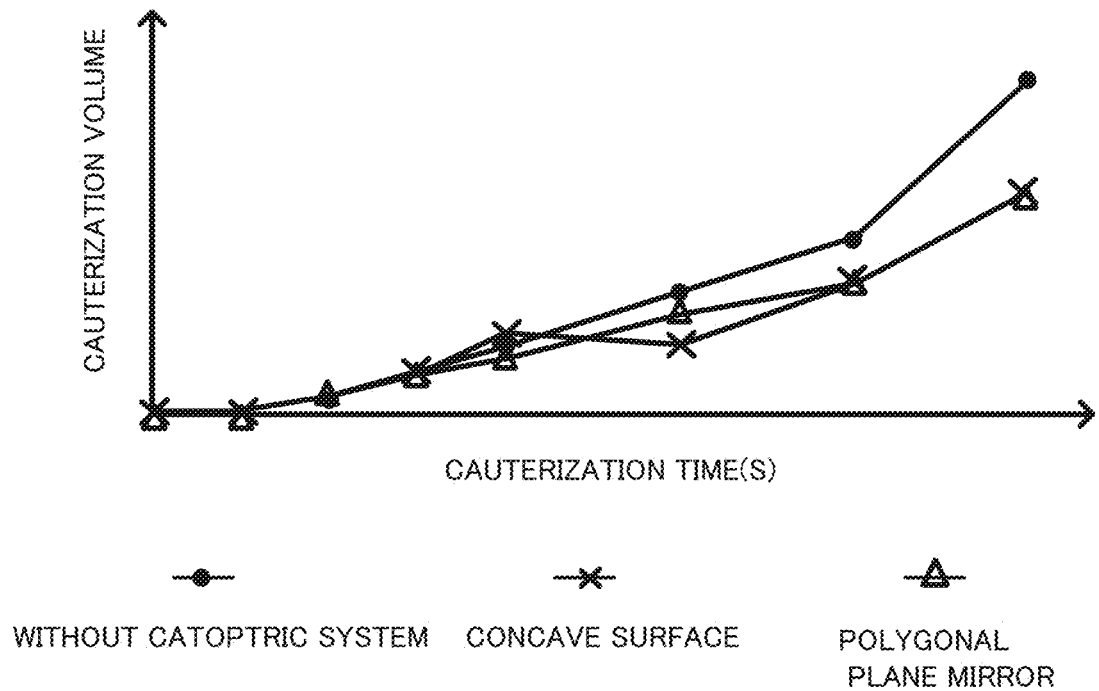
FIG. 24 is a graph illustrating changes in a cauterization volume with respect to cauterization time.

Further, as illustrated in FIG. 24, changes in a cauterization volume of the biological tissue PL also change parabolically with respect to cauterization time in the case of using the polygonal plane mirror, similarly to the case of using the concave surface; and the rate of change is almost the same. The characteristics depicted in FIG. 23 and FIG. 24 indicate that use of the polygonal plane mirror in the light radiating device 1G also enables solidification or cauterization of the biological tissue PL, similarly to the light radiating device with the reflection surface being a concave surface.

Figure 25:
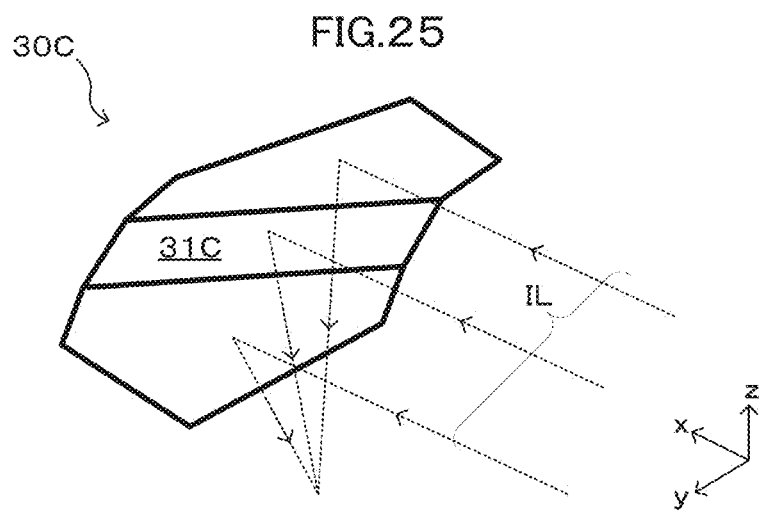
FIG. 25 is a perspective view illustrating a shape (1) of a reflection surface of a catoptric system.

Various reflection surfaces may be employed as the reflection surface 31C of the light radiating device 1G according to the present embodiment. For example, a concave reflection surface formed by connecting three planes the normal line directions of which are different from one another can be employed, as illustrated in FIG. 25. Thus, the shape of the reflection surface 31C can be further approximated to a curved surface, and therefore a degree of condensation of a light beam (light ray IL) with respect to the y-axis direction can be enhanced.

Figure 26:
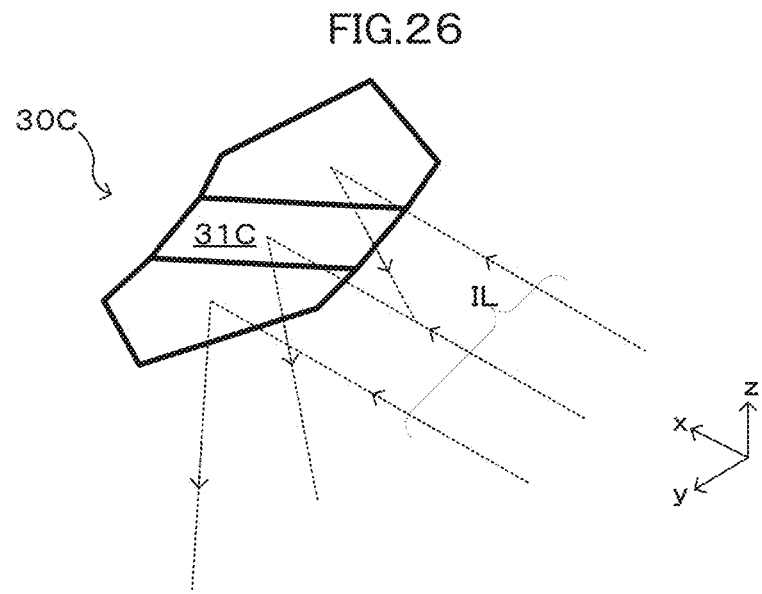
FIG. 26 is a perspective view illustrating a shape (2) of the reflection surface of the catoptric system.

Further, the shape of the reflection surface 31C of the light radiating device 1G according to the present embodiment may be formed convex with respect to the y-axis direction by connecting three planes the normal line directions of which are different from one another, as illustrated in FIG. 26. Thus, the shape of the reflection surface 31C is not limited to concave or convex. For example, the shape of the reflection surface 31C may be a parabolic surface.

Figure 27:
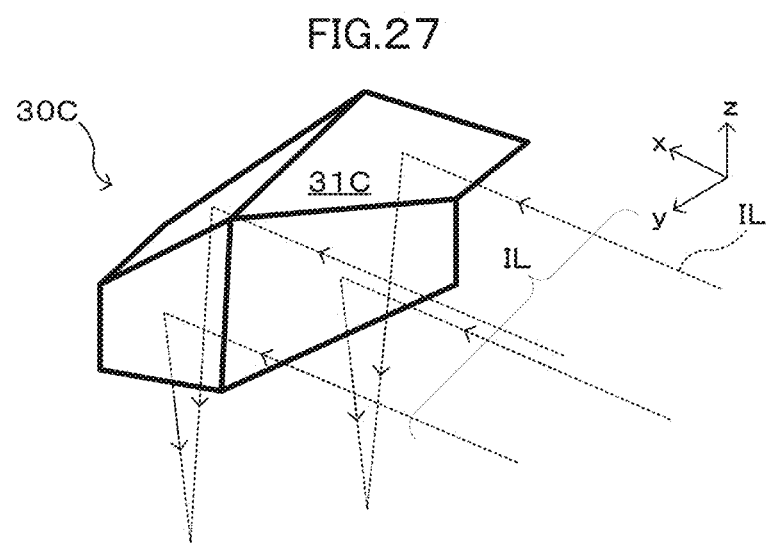
FIG. 27 is a perspective view illustrating a shape (3) of the reflection surface of the catoptric system.

Further, the section of the reflection surface 31C when the reflection surface 31C is cut by the y-z plane orthogonal to the optical axis AX1 of the optical waveguide 20E (x-axis direction) may be a concave polygonal line, as illustrated in FIG. 27. Thus, a light ray IL in the x-axis direction as well as the y-axis direction can be reflected off the reflection surface 31C, and a light ray IL traveling in a z-axis direction can be condensed. Further, the section of the reflection surface 31C may be a convex polygonal line. In this case, three planes the normal line directions of which are different may be connected or the polygonal line may be concave, in the x-axis direction.

Embodiment 8

Figure 28:
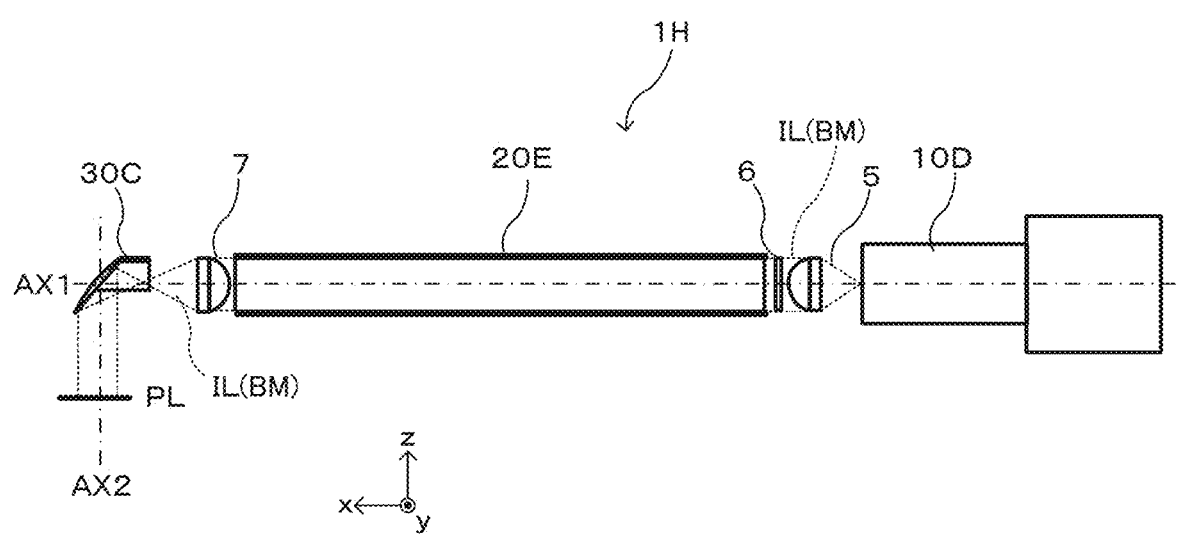
FIG. 28 is a diagram illustrating the structure of the light radiating device according to Embodiment 7 of the present disclosure.

Next, Embodiment 8 of the present disclosure will be described. As illustrated in FIG. 28, a light radiating device 1H according to the present embodiment includes a light source 10D, an optical waveguide 20E, and a catoptric system 30C. The light radiating device 1H further includes a first optical condensing system 5, a filter 6, and a second optical condensing system 7. In FIG. 28, FIG. 29, FIG. 30A, FIG. 30B, FIG. 31, and FIG. 32, the light source 10D and the optical waveguide 20E are depicted as a section including an optical axis AX1 and being parallel to an x-z plane.

Figure 29:
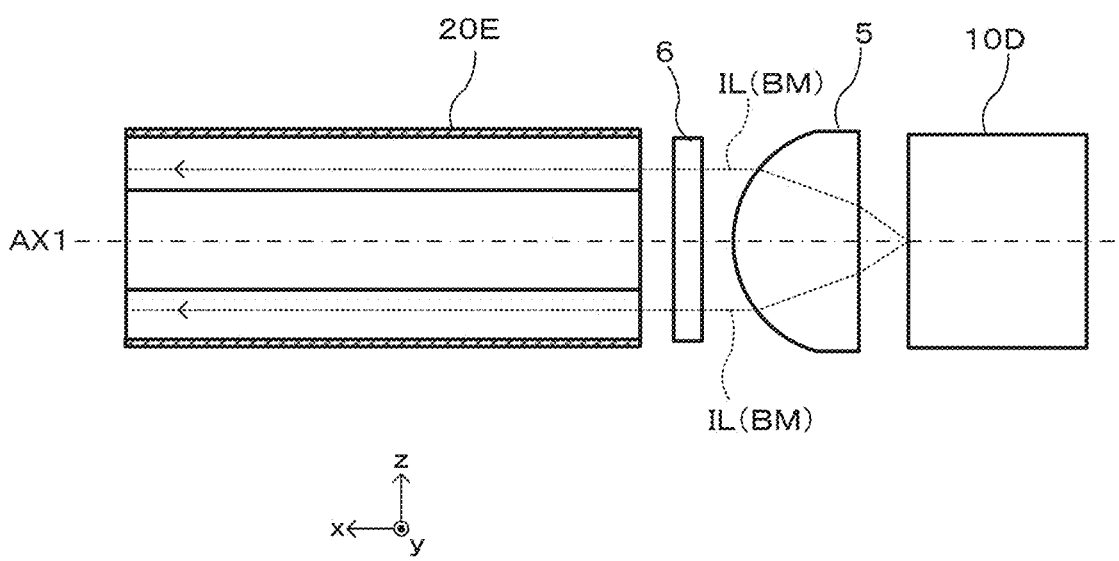
FIG. 29 is a diagram illustrating a structure around a first optical condensing system.

The light source 10D is a light guide including a plurality of optical fibers. The first optical condensing system 5 condenses a light beam BM emitted from the light source 10D and causes the light beam BM to enter at one end of the optical waveguide 20E. As illustrated in FIG. 29, the light beam BM emitted from the light source 10D becomes diffused light. The first optical condensing system 5 condenses the diffusing light beam BM and converts the light beam BM to a light beam BM closer to parallel light. The number of reflections of a light ray IL included in the light beam BM in the optical waveguide 20E can be thereby reduced, and a decline in intensity of the light ray IL can be suppressed.

The filter 6 eliminates light in the visible region from the light beam BM emitted from the first optical condensing system 5. For example, eyes of an operator in an operating room, or the like can be thereby protected as much as possible.

Figure 30A:
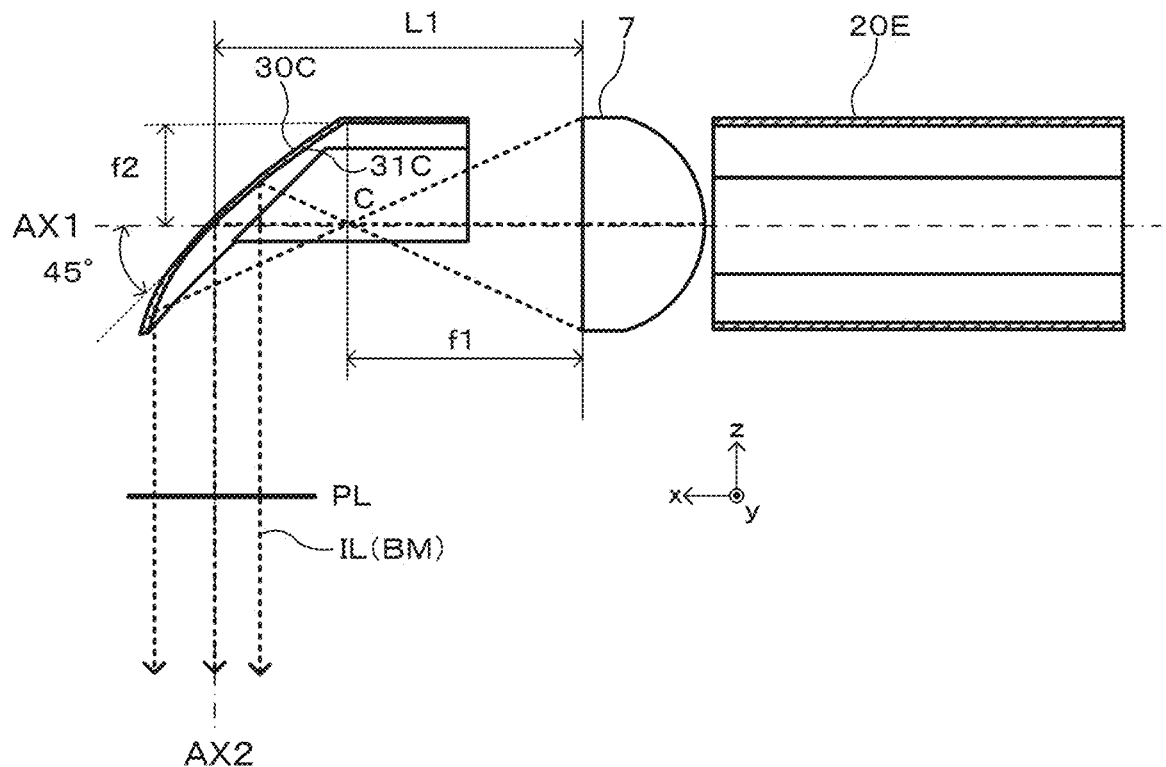
FIG. 30A is a diagram illustrating a structure around a second optical condensing system.

As illustrated in FIG. 30A, the second optical condensing system 7 condenses the light beam BM emitted from the other end of the optical waveguide 20E and causes the light beam BM to enter the catoptric system 30C. In this case, a distance L1 between the catoptric system 30C and the second optical condensing system 7 is set to be greater than a focal distance f1 of the second optical condensing system 7.

In this case, the light beam BM entering a reflection surface 31C of the catoptric system 30C becomes diffused light or condensed light. Therefore, the light beam BM reflected off the catoptric system 30C is closer to a parallel light beam compared with the light radiating device 1A (see FIG. 3) not being provided with the second optical condensing system 7. The above means that intensity of the light beam BM is uniform over a wide range with respect to a direction of an optical axis AX2. Extending, in a direction with respect to the optical axis AX2 direction, the range in which intensity of the light beam BM is uniform can facilitate adjustment of a biological tissue PL to the range.

When the sectional shape of the concave reflection surface 31C when the reflection surface 31C is cut by an incidence plane of a light ray IL entering along the optical axis AX1 of the optical waveguide 20E is approximated to a parabola, the reflection surface 31C is placed in such a way that a focus position C of the second optical condensing system 7 matches a focus f2 of the parabola, and a tilt angle of the reflection surface 31C with respect to the optical axis AX1 is set to 45°, light rays IL reflected off the reflection surface 31C become parallel light parallel to the optical axis AX2. When the tilt angle of the optical axis AX1 with respect to the reflection surface 31C is not set to 45°, light reflected off the reflection surface 31C does not become parallel to the optical axis AX2 but can be brought close to parallel light along the optical axis AX2.

Figure 30B:
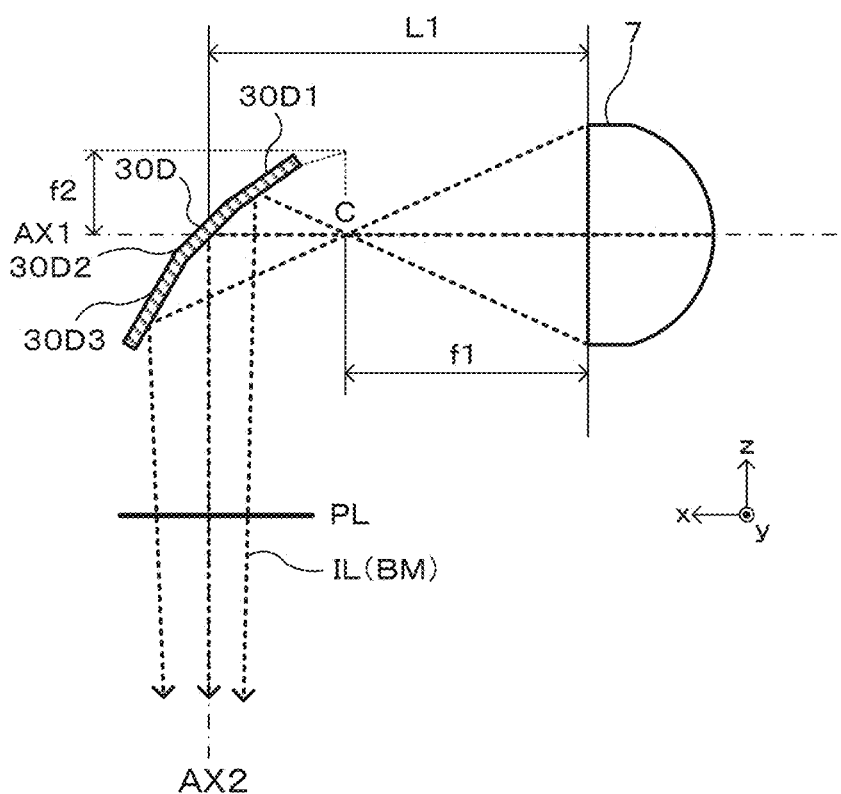
FIG. 30B is a diagram illustrating a modified example of the structure around the second optical condensing system.

Further, when the catoptric system 30C is substituted with a catoptric system 30D formed by connecting three plane mirrors 30D1, 30D2, and 30D3, as illustrated in FIG. 30B, light rays IL reflected off the catoptric system 30D do not strictly become parallel light but can be brought close to parallel light along the optical axis AX2.

Figure 31:
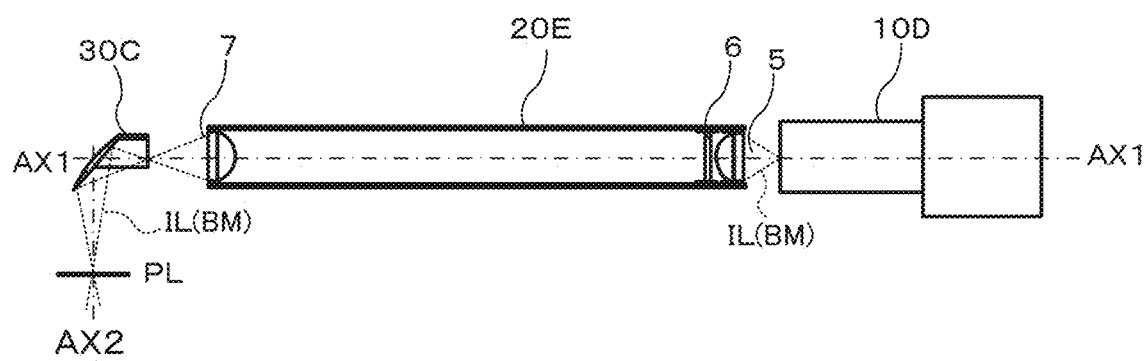
FIG. 31 is a diagram illustrating a modified example of the structure of the light radiating device according to Embodiment 7 of the present disclosure.

The first optical condensing system 5, the filter 6, and the second optical condensing system 7 may be provided inside the optical waveguide 20E, as illustrated in FIG. 31. However, when the effective diameter of the light beam BM emitted from the light source 10D is large, the entire light beam BM emitted from the light source 10D can be guided into the optical waveguide 20E by providing the first optical condensing system 5 and the like outside the optical waveguide 20E and setting the effective diameter of the first optical condensing system 5 larger than the effective diameter of the light beam BM.

Further, while the light beam BM includes light at various wavelengths including an infrared radiation, optical paths of light rays IL in the first optical condensing system 5 and the second optical condensing system 7 vary with wavelength of the light. Therefore, out of light rays IL, only light at a specific useful wavelength such as an infrared ray is reflected off the catoptric system 30C and becomes parallel light. Consequently, attenuation of light at a specific useful wavelength can be kept to a minimum.

Figure 32:
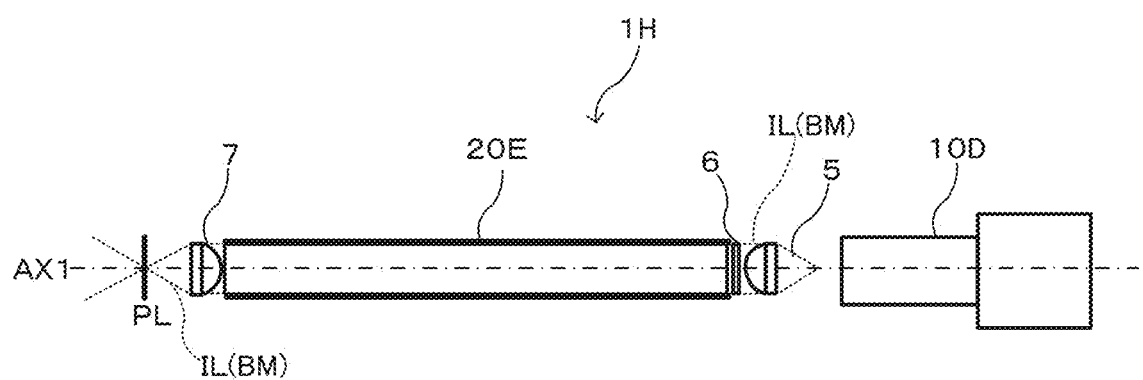
FIG. 32 is a diagram illustrating a structure of the light radiating device in FIG. 28 when a catoptric system is removed.

Furthermore, the catoptric system 30C may be attachable and detachable. By removing the catoptric system 30C as illustrated in FIG. 32, a light ray IL can be condensed on the optical axis AX1 of the optical waveguide 20E. Placing a biological tissue PL at the condensation position allows solidification or cauterization of the biological tissue PL.

FIG. 23 and FIG. 24 respectively illustrate changes in a cauterization depth with respect to cauterization time and changes in a cauterization volume with respect to cauterization time in a case of removing the catoptric system 30C. As illustrated in FIG. 23, the changes in a cauterization depth with respect to cauterization time change parabolically. The rate of change is greater compared with the case of using the catoptric system 30C. Further, as illustrated in FIG. 24, the changes in a cauterization volume with respect to cauterization time also change parabolically. The rate of change is greater compared with the case of using the catoptric system 30C.

Figure 33:
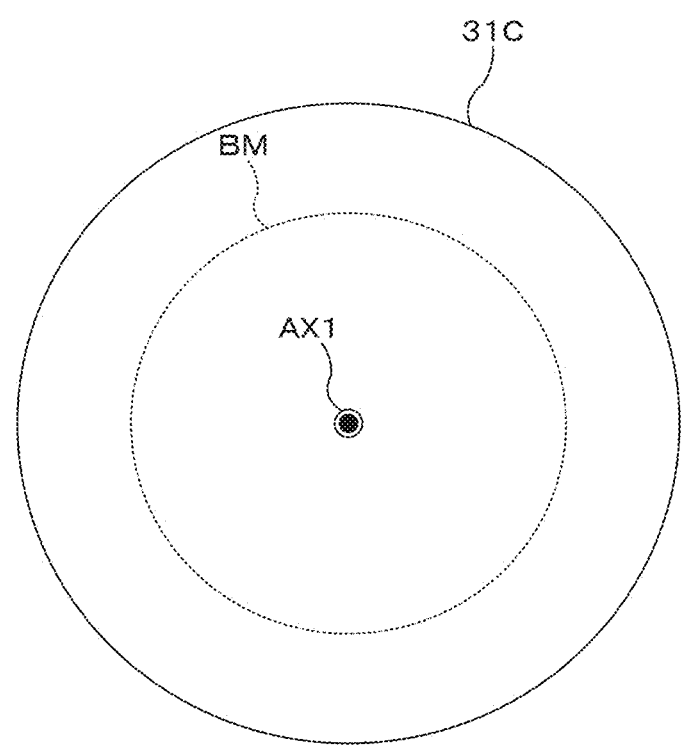
FIG. 33 is a schematic diagram illustrating a relation between the catoptric system and a light beam BM emitted from an optical waveguide.

The size of the reflection surface 31C of the catoptric system 30C when the reflection surface 31C is viewed from the optical axis AX1 direction of the optical waveguide 20E is greater than the size of the section of the light beam BM emitted from the optical waveguide 20E, as illustrated in FIG. 33. Thus, the light beam BM emitted from the optical waveguide 20E can be entirely reflected off the catoptric system 30C. The above is normally achieved by causing the size of the reflection surface 31C of the catoptric system 30C when the reflection surface 31C is viewed from the optical axis AX1 direction to be greater than the size of the section of the optical waveguide 20E when the optical waveguide 20E and the catoptric system 30C are placed in proximity to each other. When the light beam BM emitted from the optical waveguide 20E is a parallel light beam, the size of the reflection surface 31C of the catoptric system 30C has only to be equal to or greater than the size of the section of the optical waveguide 20E orthogonal to the optical axis AX1.

The light source 10D, the optical waveguide 20E or the catoptric system 30C according to the present embodiment may be replaced by that used in another embodiment, or when the light beam of the light source 10D is close to parallel light, the first optical condensing system 5 may be eliminated, and only the second optical condensing system 7 may be included.

As described in detail above, the catoptric system 30A reflecting and condensing the light beam BM sent to the other end of the optical waveguide 20A, or the like is included in each of the aforementioned embodiments. Thus, a position where light is condensed by the catoptric system 30A is intensely heated, and solidification or cauterization of a biological tissue PL can be performed at the position where light is condensed. Consequently, solidification or cauterization of the biological tissue PL at a focus F or in a region AR can be performed in a state of keeping the light radiating device 1A or the like apart from the biological tissue PL without the light radiating device 1A or the like being in tight contact with the biological tissue PL.

According to each of the aforementioned embodiments, the sectional shape of the light beam BM can be converted into point-like (focus F), linear (region AR), or the like according to the shape of the reflection surface 31A of the catoptric system 30A or the like. Thus, the sectional shape of the light beam BM can be adjusted to the shape of a tissue to be solidified or cauterized, and therefore light can be radiated only to a biological tissue PL to be treated, and efficient treatment can be provided.

According to each of the aforementioned embodiments, light in the infrared region having high transmissivity for a biological tissue PL of a human or an animal is used, and therefore solidification or cauterization can be performed down to a deep spot in the biological tissue PL.

According to each of the aforementioned embodiments, an affected part can be treated in a state of the device being kept apart from the affected part, and therefore a high degree of skill and experience, such as adjustment of a pressing force on the affected part, is not required when the light radiating device 1A or the like is used.

While a tubular member or a quartz rod is used as the optical waveguide according to each of the aforementioned embodiments, the present disclosure is not limited thereto. An optical fiber or a bundle of optical fibers may be used as the optical waveguide.

Further, while the sectional shape of the optical waveguide in a prismatic shape is a hexagon, according to the aforementioned embodiment, the present disclosure is not limited thereto. The shape may be a triangle, a rectangle, a pentagon, or a polygon with seven angles or more.

While the sectional shape of each of the reflection surfaces 31A and 31B of the catoptric systems 30A and 30B with respect to the optical axis AX1 direction of the optical waveguides 20A and 20B is set to the elliptical arc 32, according to each of the aforementioned embodiments, the present disclosure is not limited thereto. The shape has only to be a concave shape allowing the light beam BM to be condensed in the optical axis AX1 direction.

Further, while an average tilt angle of each of the reflection surfaces 31A and 31B of the catoptric systems 30A and 30B with respect to the optical axis AX1 is set to about 45 degrees, according to each of the aforementioned embodiments, the present disclosure is not limited thereto. The average tilt angle may be other than 45 degrees.

While the light beam BM emitted from each of the light sources 10A and 10B is set to light in the infrared region, according to each of the aforementioned embodiments, the present disclosure is not limited thereto. The light beam BM may be light in a wavelength region other than the infrared region. Further, the light beam BM may include light at wavelengths in the infrared region and another band.

Further, each of the light radiating device 1A and the like is assumed to be an optical scalpel performing solidification or cauterization of a biological tissue PL, according to each of the aforementioned embodiments, the present disclosure is not limited thereto. A radiation target may not be a biological tissue PL and may be another material, whether organic or inorganic.

Further, while a surface formed by depositing a metal material such as aluminum is used as the reflection surface 21A of each of the optical waveguides 20A to 20E or the like, according to each of the aforementioned embodiments, the present disclosure is not limited thereto. A metal material film surface formed by adhering a metal material by sputtering may be used as the reflection surface 21A. The reflection surface 21A has only to be a metal material film surface formed of a metal material, and a manufacturing method thereof is not limited.

Figure 34A:
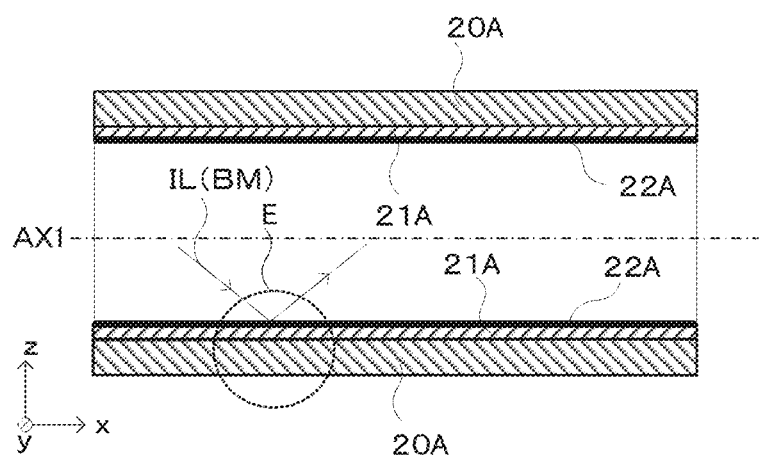
FIG. 34A is a cross-sectional view illustrating a modified example of a reflection surface.

Furthermore, a reflection control film 22A made up of silicon dioxide ($SiO_2$) may be formed on the reflection surface 21A, as illustrated in FIG. 34A. Silicon dioxide has a relatively high surface reflectance and also has relatively high transmissivity for infrared light, and therefore the reflection control film 22A can suppress attenuation of the light beam BM due to reflection off the reflection surface 21A.

Figure 34B:
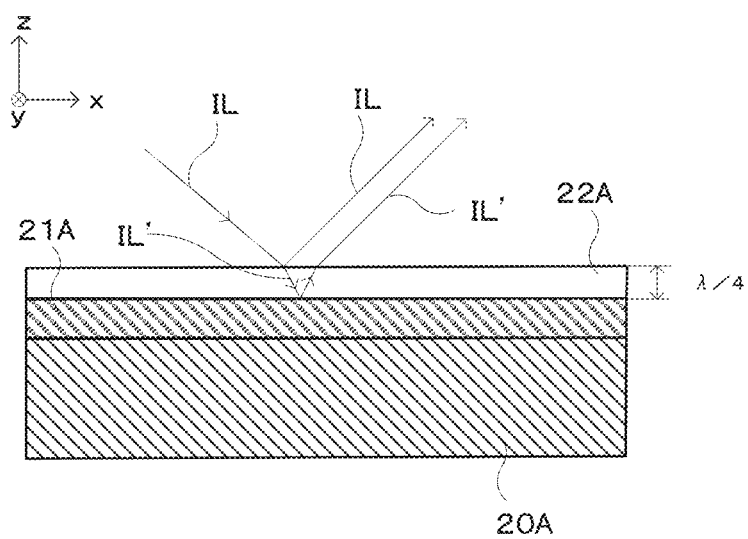
FIG. 34B is an expanded sectional view of a part E of the reflection surface in FIG. 34A.

Further, the thickness of the reflection control film 22A may be set to ¼ of a wavelength $\lambda$ of a part of light rays IL included in the light beam BM emitted from the light source 10A or 10B, that is, $\lambda/4$, as illustrated in FIG. 34B. For example, the part of light rays is a light ray at an unnecessary wavelength not contributing to heat generation in a radiation target PL. In this case, reflection intensity of a light ray IL at a specific wavelength $\lambda$ (such as a blue light ray or a green light ray) out of light rays IL radiated to the radiation target PL can be reduced by an action described below.

Specifically, part of a light ray IL at a wavelength $\lambda$ included in the light beam BM emitted from the light source 10A or 10B passes through the reflection control film 22A as a light ray IL' and is reflected off the reflection surface 21A; and the remainder is reflected off the surface of the reflection control film 22A as the light ray IL. The light ray IL' passing through the reflection control film 22A has a phase opposite to that of the light ray IL reflected off the surface of the reflection control film 22A and is combined with the light ray IL reflected off the surface of the reflection control film 22A; and the two rays cancel each other out. Consequently, intensity of the light ray IL at the specific wavelength $\lambda$ can be lowered compared with light rays IL at other wavelengths in the light beam BM radiated to the radiation target PL. Thus, providing the reflection control film 22A made up of $SiO_2$ allows the optical waveguides 20A to 20E to have a filtering function of suppressing intensity of a light ray IL at a specific wavelength $\lambda$.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

This application claims the benefit of Japanese Patent Application No. 2018-137030, filed on Jul. 20, 2018, the entire disclosure of which is incorporated by reference herein.

INDUSTRIAL APPLICABILITY

The present disclosure is applicable to solidification or cauterization of a biological tissue or the like being a radiation target.

REFERENCE SIGNS LIST 1A, 1B, 1C, 1D, 1E, 1F, 1G, 1H Light radiating device (optical scalpel)
5 First optical condensing system
6 Filter
7 Second optical condensing system
10A, 10B, 10C, 10D Light source
20A, 20B, 20C, 20D, 20E Optical waveguide
21A Reflection surface
22A Reflection control film
30A, 30B, 30C, 30D Catoptric system
30C1, 30C2, 30D1, 30D2, 30D3 Plane mirror
31A, 31B, 31C Reflection surface
31C1, 31C2 Reflection surface
32 Elliptical arc
33, 34 Circular arc
40 Optical fiber
50 Heat insulating part
51 Exterior cover
52 Spacer
53 Projection
54 Through hole
60 Operation device
61 Grip 62 Switch
65 Shutter
80 Optical fiber
AR Region
AX1, AX2 Optical axis
BM Light beam
CL Curve
DL Connecting line
F Focus
IL, IL' Light ray
IP1 Incidence plane
IP2 Plane
P Incidence position
PL Biological tissue (radiation target)
P1 First position
P2 Second position

The invention claimed is:

1. A light radiating device performing solidification or cauterization of a radiation target by radiating a light beam, the light radiating device comprising:
a light source emitting the light beam;
an optical waveguide including a tubular hollow member having an inner circumferential side wall extending between a first end and a second end along a first optical axis and provided with a first reflection surface including a metal material film formed on the inner circumferential side wall totally reflecting the light beam, causing the light beam emitted from the light source to enter a part enclosed by the inner circumferential side wall from the first end, and sending the light beam to the second end along the first optical axis; and
a catoptric system reflecting the light beam sent to the second end of the optical waveguide and condensing the light beam on the radiation target;
wherein the catoptric system includes a second reflection surface having two different sectional shapes including:
a first sectional shape defined along a first axis and including a concave elliptical am defined by an ellipse having a major axis defined along the first optical axis and configured to condense light rays entering each point on the concave elliptical arc onto a focus of the concave elliptical arc defined along a second optical axis orthogonal to the first optical axis; and
a second sectional shape defined along a second axis perpendicular to the first axis and including a concave circular arc including a radius such that light rays entering each point on the concave circular arc are condensed onto the focus of the concave elliptical arc defined along the second optical axis;
wherein the optical waveguide is configured to reflect a light ray along the first optical axis at a first reflected position along the inner circumferential side wall and at a second reflected position along the inner circumferential side wall after being reflected at the first reflected position at a maximum emission angle of 30 degrees; and
wherein the light radiating device includes a length defined between the light source and an incidence position defined on the second reflection surface of the catoptric system of a light ray entering along the first optical axis of the optical waveguide that is equal to four times a distance defined between the first reflected position and the second reflected position.

2. The light radiating device according to claim 1, wherein the second reflection surface of the catoptric system includes a metal film deposited on an enclosure.

3. The light radiating device according to claim 2, wherein the enclosure is formed of metal or resin.

4. The light radiating device according to claim 2, wherein the metal film is aluminum.

5. The light radiating device according to claim 1, wherein a film made up of silicon dioxide is formed on a surface of the metal material film.

6. The light radiating device according to claim 5, wherein a thickness of the film made up of silicon dioxide is ¼ of a wavelength of a part of one or more light rays included in the light beam emitted from the light source.

7. The light radiating device according to claim 1, wherein the inner circumferential side wall is formed in a prismatic shape in the optical waveguide.

8. The light radiating device according to claim 1, wherein a heat insulating part is provided on an outer periphery of the optical waveguide and the catoptric system.

9. The light radiating device according to claim 8, wherein the heat insulating part includes:
an exterior cover enclosing an outer periphery of the optical waveguide and the catoptric system; and
a spacer inserted between the optical waveguide and the catoptric system, and the exterior cover in order to provide a gap between the optical waveguide and the catoptric system, and the exterior cover.

10. The light radiating device according to claim 9, wherein, on the spacer, a plurality of projections is provided on at least one of a part facing the optical waveguide and the catoptric system, and a part facing the exterior cover.

11. The light radiating device according to claim 1, wherein a size of the second reflection surface of the catoptric system when the second reflection surface is viewed from a direction of the first optical axis of the optical waveguide is equal to or greater than a size of a section of the light beam entering the catoptric system from the optical waveguide.

12. The light radiating device according to claim 1, wherein the light beam emitted from the light source includes an infrared radiation.

13. The light radiating device according to claim 12, wherein the light source is one of a halogen lamp, a xenon lamp, an infrared heater, and an infrared laser.

* * * * *